(12) United States Patent
Murray et al.

(10) Patent No.: US 10,753,945 B2
(45) Date of Patent: *Aug. 25, 2020

(54) ISOTYPING IMMUNOGLOBULINS USING ACCURATE MOLECULAR MASS

(71) Applicant: Mayo Foundation for Medical Education and Research, Rochester, MN (US)

(72) Inventors: David L. Murray, Rochester, MN (US); David R. Barnidge, Rochester, MN (US); Surendra Dasari, Rochester, MN (US); John R. Mills, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/297,340

(22) Filed: Mar. 8, 2019

(65) Prior Publication Data

US 2020/0003784 A1 Jan. 2, 2020

Related U.S. Application Data

(63) Continuation of application No. 15/301,633, filed as application No. PCT/US2015/024379 on Apr. 3, 2015, now Pat. No. 10,267,806.

(60) Provisional application No. 61/975,524, filed on Apr. 4, 2014.

(51) Int. Cl.
*G01N 33/68* (2006.01)
*G01N 30/72* (2006.01)

(52) U.S. Cl.
CPC ..... *G01N 33/6848* (2013.01); *G01N 30/7266* (2013.01); *G01N 33/6857* (2013.01); *G01N 2800/52* (2013.01); *G01N 2800/7095* (2013.01)

(58) Field of Classification Search
None
See application file for complete search history.

(56) References Cited

U.S. PATENT DOCUMENTS

| 8,501,907 B2 | 8/2013 | Jordan et al. |
| 8,679,767 B2 | 3/2014 | Kaur et al. |
| 2002/0182649 A1 | 12/2002 | Weinberger et al. |
| 2003/0027216 A1 | 2/2003 | Kiernan et al. |
| 2005/0009009 A1 | 1/2005 | Peiris et al. |
| 2005/0064422 A1 | 3/2005 | Barnidge et al. |
| 2006/0024296 A1 | 2/2006 | Williams |

(Continued)

FOREIGN PATENT DOCUMENTS

| WO | WO 2006138629 | 12/2006 |
| WO | WO 2013096451 | 6/2013 |

(Continued)

OTHER PUBLICATIONS

Barnidge and Murray, "Using Mass Spectrometry to Identify IgG Fc and Fab Fragments Produced by Plasmin in Patient Serum," Poster, Presented at American Society for Mass Spectrometry meeting on Jun. 7, 2016.

(Continued)

*Primary Examiner* — Xiaoyun R Xu
(74) *Attorney, Agent, or Firm* — Fish & Richardson P.C.

(57) ABSTRACT

This document relates to methods for detecting and quantifying heavy and light chains of immunoglobulin using mass spectrometry techniques.

20 Claims, 21 Drawing Sheets

Specification includes a Sequence Listing.

(56) References Cited

U.S. PATENT DOCUMENTS

| | | |
|---|---|---|
| 2006/0281122 A1 | 12/2006 | Bryant |
| 2007/0184470 A1 | 8/2007 | Aman et al. |
| 2007/0259398 A1 | 11/2007 | Arnott et al. |
| 2007/0292441 A1 | 12/2007 | Glover et al. |
| 2008/0064055 A1 | 3/2008 | Bryant |
| 2008/0142696 A1 | 6/2008 | Geromanos et al. |
| 2008/0317745 A1 | 12/2008 | Boruchov et al. |
| 2009/0186423 A1 | 7/2009 | Frandsen |
| 2009/0203602 A1 | 8/2009 | Gelber et al. |
| 2010/0086922 A1 | 4/2010 | Bryant |
| 2010/0323381 A1 | 12/2010 | Bergen, III et al. |
| 2011/0117021 A1 | 5/2011 | Smith et al. |
| 2011/0151494 A1 | 6/2011 | Koomen et al. |
| 2012/0315645 A1 | 12/2012 | Kaur et al. |
| 2012/0322073 A1 | 12/2012 | Lopez-Girona |
| 2013/0185096 A1 | 7/2013 | Giusti |
| 2014/0045276 A1 | 2/2014 | Singh et al. |
| 2014/0186332 A1 | 7/2014 | Ezrin et al. |
| 2014/0242072 A1 | 8/2014 | Hansson |
| 2014/0242624 A1 | 8/2014 | Valliere-Douglass |
| 2015/0204884 A1 | 7/2015 | Robblee |
| 2015/0340219 A1 | 11/2015 | Mellors |
| 2016/0041184 A1 | 2/2016 | Barnidge et al. |
| 2016/0206660 A1 | 7/2016 | Shi et al. |
| 2016/0257763 A1 | 9/2016 | Von Kreudenstein et al. |
| 2017/0023584 A1 | 1/2017 | Murray et al. |
| 2018/0106815 A1 | 4/2018 | Barnidge et al. |
| 2018/0267057 A1 | 9/2018 | Barnidge et al. |
| 2019/0195888 A1 | 6/2019 | Barnidge et al. |

FOREIGN PATENT DOCUMENTS

| | | |
|---|---|---|
| WO | WO 2014109927 | 7/2014 |
| WO | WO 2014150170 | 9/2014 |
| WO | WO 2015154052 | 10/2015 |
| WO | WO 2016018978 | 2/2016 |
| WO | WO 2017022315 | 2/2017 |

OTHER PUBLICATIONS

Bastian et al., "Intra- and interchain disulfide bridges of the human J chain in secretory immunoglobulin A," Biol. Chem. Hoppe Seyler., 373(12):1255-63, Dec. 1992.

Chevreux et al., "Fast analysis of recombinant monoclonal antibodies using IdeS proteolytic digestion and electrospray mass spectrometry," Analytical Biochemistry, 415(2):212-214, Aug. 2011.

De Lorenzi et al., "Urokinase links plasminogen activation and cell adhesion by cleavage of the RGD motif in vitronectin," EMBO reports, 17(7):982-98, Jul. 2016.

Drożdżet al., "Immunoglobulin cleavage by hypochlorous acid treatment," Clinica. Chimica. acta., 236(2):155-60, May 1995.

Faca et al., "Innovative proteomic approaches for cancer biomarker discovery," Biotechniques, 43(3):279-283, Sep. 2007.

Gadgil et al., "The LC/MS analysis of glycation of IgG molecules in sucrose containing formulations," Journal of Pharmaceutical Sciences, 96(10):2607-2621, Oct. 2007.

Hanash et al., "Mining the plasma proteome for cancer biomarkers," Nature, 452(7187)571-579, Apr. 2008.

Huse et al., "Purification of antibodies by affinity chromatography," Journal of biochemical and biophysical methods, 51(3):217-31, May 2002.

Kleennann et al., "Characterization of IgG1 immunoglobulins and peptide-Fc fusion proteins by limited proteolysis in conjunction with LC-MS," Analytical Chemistry, 80(6):2001-2009, Mar. 2008.

Kragten et al., "Site-specific analysis of the N-glycans on murine polymeric immunoglobulin A using liquid chromatography/electrospray mass spectrometry," Journal of Mass Spectrometry, 30(12):1679-86, Dec. 1995.

Legros et al., "Characterization of an anti-Borrelia burgdorferi OspA conformational epitope by limited proteolysis of monoclonal antibody-bound antigen and mass spectrometric peptide mapping," Protein Science, 9(5):1002-10, May 2000.

Mazur et al., "A platform for characterizing therapeutic monoclonal antibody breakdown products by 2D chromatography and top-down mass spectrometry," The AAPS journal, 14(3):530-41, Sep. 2012.

Mills et al., "Using mass spectrometry to quantify rituximab and perform individualized immunoglobulin phenotyping in ANCA-associated vasculitis," Analytical chemistry, 88(12):6317-25, Jun. 2016.

Qin et al., "Development of a "reverse capture" autoantibody microarray for studies of antigen-autoantibody profiling," Proteomics., 6(10):3199-209, May 2006.

Reid et al., "Rapid whole monoclonal antibody analysis by mass spectrometry: An ultra scale-down study of the effect of harvesting by centrifugation on the post-translational modification profile," Biotechnology and Bioengineering, 107(1):85-95, Sep. 2010.

Sun et al., "Preparation and mass spectrometric study of egg yolk antibody (IgY) against rabies virus," Rapid communications in mass spectrometry, 15(9):708-12, May 2001.

Vrana et al., "Classification of amyloidosis by laser microdissection and mass spectrometry-based proteomic analysis in clinical biopsy specimens," Blood, 114(24):4957-4960, Dec. 2009.

Aisina and Mukhametova, "Structure and Function of Plasminogen/Plasmin System," Russian Journal of Bioorganic Chemistry, 40(6):590-605, Nov. 2014.

Attealnnannan and Levinson et al., "Understanding and Identifying monoclonal gammopathies," Clinical Chemistry, Aug. 2000, 46(8B):1230-1238.

Hutchison et al., "The pathogenesis and diagnosis of acute kidney injury in multiple myeloma," Nature Reviews Nephrology, Jan. 2012, 8:43-51.

Kiselar et al., "Direct Identification of Protein Epitopes by Mass Spectrometry Without Immobilization of Antibody and Isolation of Antibody-Peptide Complexes," Analytical Chemistry, May 1999, 71(9):1792-1801.

Kissel andMendell, "Neuropathies associated with monoclonal gammopathies," Neuromuscular disorders, Jan. 1996, 6(1):3-18.

Lim et al., "Identification and Location of a Cysteinyl Post-translational Modification in an Amyloidogenic kappal Light Chain Protein by Electrospray Ionization and Matrix-Assisted Laser Desorption/Ionization Mass Spectrometry," Analytical Biochemistry, Aug. 2001, 295:45-56.

Markowitz, "Dysproteinemia and the Kidney," Advances in Anatomic Pathology, Jan. 2004, 11:49-63.

Mischak et al., "Urinary proteome analysis using capillary electrophoresis coupled to mass spectrometry: a powerful tool in clinical diagnosis, prognosis and therapy evaluation," Journal of Medical Biochemistry, Oct. 2009, 28(4):223-234.

Persson et al., "Development of Mass Spectrometry Based Techniques for the Identification and Determination of Compositional Variability in Recombinant Polyclonal Antibody Products," Analytical Chemistry, Sep. 2010, 82(17):7274-7282.

Roberts et al., "An Integrated Strategy for Structural Characterization of the Protein and Carbohydrate Components of Monoclonal Antibodies: Application to Anti-Respiratory Syncytial Virus Mab," Analytical Chemistry, Oct. 1995, 67(20):3613-3625.

Shaheen et al., "Multiple Myeloma and Immunosecretory Disorders: An Update," Advances in Anatomic Pathology, Jul. 2008, 15(4):196-210.

Sikkink et al., "Biochemical and Aggregation Analysis of Bence Jones Proteins From Different Light Chain Diseases," Amyloid, Mar. 2008, 15:29-39.

Wang et al., "Structural Characterization of a Recombinant Monoclonal Antibody by Electrospray Time-of-Flight Mass Spectrometry," Pharmaceutical Research, Aug. 2005, 22(8):1338-1349.

Extended European Search Report in European Application No. 15772546.6 dated Dec. 3, 2018, 208 pages.

Wagner-Rousset et al., "The way forward, enhanced characterization of therapeutic antibody glycosylation: comparison of three level mass spectrometry-based strategies," Journal of Chromatography B, 872(1-2):23-37, Sep. 2008.

(56) References Cited

OTHER PUBLICATIONS

Wang et al., "Molecular basis of assembly and activation of complement component C1 in complex with immunoglobulin G1 and antigen," Molecular cell, 63(1):135-45, Jul. 2016.

Wine, Y. et al. Molecular deconvolution of the monoclonal antibodies that comprise the polyclonal serum response, PNAS vol. 110, No. 8, pp. 2993-2998 (Year: 2013).

Yamazaki et al., "A proteolytic modification of AIM promotes its renal excretion," Scientific Reports, 6:38762, Dec. 2016.

Abca3:74m, "Understanding secondary antibodies" 2012, 12 pages, downloaded from http://docs.abcam.com/pdf/general/understanding_secondary_antibodies.pdf.

Abraham et al., "Characterization of free immunoglobulin light chains (LC) by mass spectrometry in light chain-associated (AL) amyloidosis," American Society of Hematology 43rd Annual Meeting, part 2, Orlando, Florida, USA, 98(11 Pt 2), p. 31b, Abstract#3722, Nov. 16, 2001.

Abraham et al., "Correlation of serum immunogslobulin free light chain quantification with urinary Bence Jones protein in light chain myeloma," Clin. Chem., 48(4):655-657, Apr. 2002.

Abraham et al., "Trimolecular complexes of lambda light chain dimers in serum of a patient with multiple myeloma," Clin Chem., 48(10):1805-1811, Oct. 2002.

Adamczyk et al., "Profiling of polyclonal antibody light chains by liquid chromatography/electrospray ionization mass spectrometry," Rapid Commun Mass Spectrom., 14:49-51, 2000.

Adamczyk et al.,"Papain digestion of different mouse lgG subclasses as studied by electrospray mass spectrometry," J Immun Methods., 237:95-104, 2000.

Alge et al., "Proteomic Analysis of Plasma Exosome-Associated Proteins Reveals That Differences in Kappa: Lambda Ratios Predict Severe Acute Graft-Versus-Host Disease Early After Allogeneic Hematopoietic Stem Cell Transplantation," Blood., 1278, Nov. 2010.

Alldridge et al., "Proteome profiling of breast tumors by gel electrophoresis and nanoscale electrospray ionization mass spectrometry," J. Proteome. Res., 7(4):1458-1469, Apr. 2008.

Anonymous: "KappaSelect LambdaFabSelect," Data File 28/9448-22 AB, Mar. 1, 2012, Retrieved from the Internet: URL: https://www.gelifesciences.co.jp/catalog/pdf/Kappaselect_LamdaFabSelect.pdf Retrieved on Sep. 22, 2017, 4 pages.

Arun et al., "Immunohistochemical examination of light-chain expression (lambda/kappa ratio) in canine, feline, equine, bovine and porcine plasma cells," Zentralbl Veterinarmed A., 43(9):573-576, Nov. 1996.

Aucouturier et al., "Monoclonal Ig L chain and L chain V domain fragment crystallization in myeloma-associated Fanconi's syndrome" J. Immunol., 150(8 Pt 1):3561-3568, Apr. 1993.

Aucouturier et al., "Monoclonal immunoglobulin light chains associated to Fanconi's syndrome," Monoclonal Gammopathies and the Kidney, 2003, 87-92.

Awad et al., "Analyses of cerebrospinal fluid in the diagnosis and monitoring of multiple sclerosis," J Neuroimmunol., 219(1-2):1-7, Epub Sep. 25, 2009.

Barnidge et al., "Monitoring free light chains in serum using mass spectrometry," Clinical Chemistry and Laboratory Medicine (CCLM). ISSN (Online) 1437-4331, ISSN (Print) 1434-6621, DOI: 10.1515/cclm-2015-0917, Feb. 2016.

Barnidge et al., "Monitoring M-proteins in patients with multiple myeloma using heavy-chain variable region clonotypic peptides and LC-MS/MS," J Proteome Res., 13(4):1905-1910, Epub Mar. 5, 2014.

Barnidge et al., "Phenotyping polyclonal kappa and lambda light chain molecular mass distributions in patient serum using mass spectrometry," J Proteome Res., 13(11):5198-5205, Epub Aug. 26, 2014.

Barnidge et al., "Using MALDI-TOF MS to Screen for Monoclonal Gammopathies in Serum and Urine," 61st Annual ASMS Conference on Mass Spectrometry and Allied Topics, Minneapolis, MN, Jun. 9-13, 2013, 1 page poster.

Barnidge et al., "Using mass spectrometry to monitor monoclonal immunoglobulins in patients with a monoclonal gammopathy," J Proteome Res., 13(3):1419-1427, Epub Feb. 11, 2014.

Barnidge, "Monitoring specific IgG tryptic peptides in multiple myeloma using the TripleTOFtm 5600 System," AB SCIEX Annual Users Meeting at ASMS, May 20, 2012, 28 slides.

Barratt et al., "Urine proteomics: the present and future of measuring urinary protein components in disease," CMAJ, 177(4):361-368, Aug. 2007.

Beck et al., "Characterization of therapeutic antibodies and related products," Anal. Chem., 85(2):715-736, Jan. 2013.

Bennett et al., "Monitoring papain digestion of a monoclonal antibody by electrospray ionization mass spectrometry," Analytical Biochemistry., 245:17-27,1997.

Berg et al., "Mass spectrometry based proteomic analysis identifies two distinct types of cutaneous amyloidosis," Mod Pathol., vol. 22; p100A, 2009.

Bergen et al., "Characterization of amyloidogenic immunoglobulin light chains directly from serum by on-line immunoaffinity isolation," Biomedical Chromatography, 18(3):191-201, Apr. 1, 2004.

Bergon et al., "Linearity and detection limit in the measurement of serum M-protein with the capillary zone electrophoresis system Capillarys," Clinical Chemistry and Laboratory Medicine, 43:721-723, 2005.

Bermudez-Crespo et al., "A better understanding of molecular mechanisms underlying human disease," Proteomics Clinical Applications, 1:983-1003, 2007.

Biosis accession No. PREV200200151435, 2 pages, Nov. 2001 Abstract only.

Biosis accession No. PREV201100424453, 2 pages, Nov. 2010 Abstract only.

Bois et al., "Cutaneous amyloidosis: mass spectrometry based proteomic analysis reveals diverse etiology associated with unique histopathological features," Mod Pathol., 26:320A-321A, Feb. 2013.

Boissinot et al., "Up-Regulation of Anti-Inflammatory, STAT3-Activating Hepatocyte Growth Factor and Interleukin-11 in Polycythemia Vera is Independent of JAK2V617F and Contributes to the Growth of Clonal Erythroblasts," Blood, 116(21):796, Nov. 2010, 52nd Annual Meeting of the American Society of Hematology, Orlando, FL, USA Dec. 4-7, 2010.

Bondarenko et al., "Mass measurement and top-down HPLC/MS analysis of intact monoclonal antibodies on a hybrid linear quadrupole ion trap-orbitrap mass spectrometer," J Am Soc Mass Spectrometry., 20:1415-1424, 2009.

Bourell et al., "Electrospray ionization mass spectrometry of recombinantly engineered antibody fragments," Anal Chem., 66:2088-2095, 1994.

Bradwell et al., "Highly sensitive, automated immunoassay for immunoglobulin free light chains in serum and urine," Clin Chem., 47(4):673-680, Apr. 2001.

Breitkopf et al., "Detection of a rare BCR-ABL tyrosine kinase fusion protein in H929 multiple myeloma cells using immunoprecipitation (IP)-tandem mass spectrometry (MS/MS)," Proc. Natl. Acad. Sci. USA., 109(40):16190-16195, Oct. 2012.

Brochet et al., "IMGT/V-Quest: the highly customized and integrated system for IG and TR standardized V-J and V-D-J sequence analysis," Nucleic Acids Res., 36(Web Server issue):W503-W508, Epub May 24, 2008.

Butler et al., "Immunoglobulins, antibody repertoire and B cell development," Dev Comp Immunol., 33(3):321-333, Epub Sep. 18, 2008.

Chen et al., "Characterization of protein therapeutics by mass spectrometry: recent developments and future directions," Drug Discovery Today., 16:58-64, 2011.

Cheung et al., "A proteomics approach for the identification and cloning of monoclonal antibodies from serum," Nature Biotechnology., 30:447-452, 2012.

Chiasserini et al., "CSF proteome analysis in multiple sclerosis patients by dimensional electrophoresis," Eur. J. Neurol., 15(9):998-1001, Sep. 2008.

Chung et al., "Thermodynamic stability of a kappal immunoglobulin light chain: relevance to multiple myeloma," Biophys. J., 88(6):4232-4242, Jun. 2005.

(56) References Cited

OTHER PUBLICATIONS

Cohen., "Antibody structure," J Clin Path., 28 Suppl, 6:1-7, 1975.
Cordoba et al., "Non-enzymatic hinge region fragmentation of antibodies in solution," J Chromatography B., 818:115-121, 2005.
Coriu et al., "A molecular basis for nonsecretory myeloma," Blood, 104(3):829-831, Aug. 2004.
D'Aguanno et al., "Differential cerebro spinal fluid proteome investigation of Leber hereditary optic neuropathy (LHON) and multiple sclerosis," 193(1-2):156-160, Dec. 2007.
Dannoc et al., "High resolution proteome analysis of cryoglobulins using Fourier transform-ion cyclotron resonance mass spectrometry," Proteomics, 3(8):1425-1433, Aug. 2003.
De Costa et al., "Sequencing and Quantifying IgG Fragments and Antigen-Binding Regions by Mass Spectrometry" Journal of Proteome Research, 9:2937-2945, Epub Apr. 14, 2010.
Dear et al., "Acquired dysfibrinogenemia caused by monoclonal production of immunoglobulin lambda light chain," Haematologica., 92(11):e111-7, Nov. 2007.
Dekker et al., "An Antibody-Based Biomamarker Discovery Method by Mass Spectrometry Sequencing of Complementarity Determining Regions," Analytical and Bioanalytical Chemistry, 399:1081-1091, 2011.
Dillon et al., "Optimization of a reversed-phase high-performance liquid chromatography/mass spectrometry method for characterizing recombinant antibody heterogeneity and stability," J. Chromatogr. A., 1120(1-2):112-20, Jul. 2006.
Dogan et al., "Leukocyte Chemotactic Factor 2 Amyloidosis: A Novel Type of Amyloidosis That Mimics AL Amyloidosis," presented at the United States and Canadian Academy of Pathology Annual Meeting, Mar. 2009, 1 page.
Extended European Search Report in Application No. 18174068.9, dated Jul. 10, 2018, 9 pages.
Extended European Search Report in European Application No. 15827198.1, dated Nov. 23, 2017, 12 pages.
Fan et al., "Identification of Niemann-Pick C1 disease biomarkers through sphingolipid profiling," J. Lipid. Res., 54(10):2800-2814, Oct. 2013.
Favereaux et al., "Serum IgG antibodies to P0 dimer and 35 kDa P0 related protein in neuropathy associated with monoclonal gammopathy," J Neurol Neurosurg Psychiatry., 74:1262-1266, 2003.
Fortini et al., "Cerebrospinal fluid oligoclonal bands in the diagnosis of multiple sclerosis. Isoelectric focusing with IgG immunoblotting compared with high-resolution agarose gel electrophoresis and cerebrospinal fluid IgG index," Am J Clin Pathol., 120(5):672-675, Nov. 2003.
Frangione, B., "Structure of Human Immuniglobulins and their Variants" B. Benacerraf (ed) Immunogenetics and Immunodeficiency, 1-53, 1975.
Gebski et al., "Affinity chromatography applications with single-domain antibodies," Bioprocess International., Aug. 1, 2013, Retrieved from the Internet: URL: http://www.bioprocessintl.com/2013/affinity-chromatography-applications-with-single-domain-antibodies-345480/ Retrieved on Sep. 22, 2017.
GenBank Accession AAA59107, "immunoglobulin lambda light chain C2 region, partial [*Homo sapiens*]," May 4, 2000, 2 pages.
Gucinski et al., "Evaluation of intact mass spectrometry for the quantitative analysis of protein therapeutics," Anal. Chem., 84(18):8045-8051, Sep. 2012.
Hagman et al., "Absolute quantification of monoclonal antibodies in biofluids by liquid chromatography-tandem mass spectrometry," Analytical Chemistry, 80(4):1290-1296, Feb. 15, 2008.
Hagmann et al., "Characterization of the F(ab')2 fragment of a murine monoclonal antibody using capillary isoelectric focusing and electrospray ionization mass spectrometry," J Chromatography A., 816:49-58, 1998.
Haraldsson et al., "Determination of kappa and lambda light chains in serum immunoglobulins G, A and M," Ann Clin Biochem., 28 (Pt 5):461-466, Sep. 1991.
Heudi et al., "Towards absolute quantification of therapeutic monoclonal antibody in serum by LC-MS/MS using isotope-labeled antibody standard and protein cleavage isotope dilution mass spectrometry," Anal Chem., 80(11):4200-4207, Epub May 9, 2008.
Hieter et al., "Clustered arrangement of immunoglobuling constant region genes in man," Nature, 294:536-540, 1981.
Hill et al., "Serum free light chains: an alternative to the urine Bence Jones proteins screening test for monoclonal gammopathies," Clin. Chem., 52(9):1743-1748, Sep. 2006.
Holding et al., "Use of serum free light chain analysis and urine protein electrophoresis for detection of monoclonal gammopathies," Clin. Chem. Lab. Med., 49(1):83-88, Jan. 2011.
Hsieh et al., "Elucidation of potential bortezomib response markers in multiple myeloma patients," Journal of Pharmaceutical and Biomedical Analysis, 49:115-122, 2009.
International Preliminary Report on Patentability for PCT/US2015/024379, dated Oct. 13, 2016, 10 pages.
International Preliminary Report on Patentability for PCT/US2015/042580, dated Jan. 31, 2017, 10 pages.
International Search Report and Written Opinion for PCT/US2015/024379, dated Aug. 25, 2015, 13 pages.
International Search Report and Written Opinion for PCT/US2016/53675, dated Feb. 28, 2017, 15 pages.
Invitation to Pay for PCT/US2015/024379, dated Jun. 25, 2015, 2 pages.
Jagannath et al., "Value of serum free light chain testing for the diagnosis and monitoring of monoclonal gammopathies in hematology," Clin Lymphoma Myeloma, 7(8):518-523, Sep. 2007.
Jemal et al., "Cancer statistics, 2003," CA Cancer J Clin., 53(1):5-26, Jan.-Feb. 2003.
Johnson et al., "Cation exchange-HPLC and mass spectrometry reveal C-terminal amidation of an IgG1 heavy chain," Anal. Biochem., 360(1):75-83, Jan. 2007.
Jones et al., "A protocol for 'enhanced pepsin digestion': a step by step method for obtaining pure antibody fragments in high yield from serum," J of Immunol Methods., 275:239-250, 2003.
Joosten et al., "The production of antibody fragments and antibody fusion proteins by yeasts and filamentous fungi," Microbial Cell Factories., 2:1, 15 pages, 2003.
Kabat et al., "An electrophoretic study of the protein components in cerebrospinal fluid and their relationship to the serum proteins," J Clin Invest., 21(5):571-577, Sep. 1942.
Kalaga et al., "Unexpected presence of polyreactive catalytic antibodies in IgG from unimmunized donors and decreased levels in rheumatoid arthritis," J. Immunol., 155(5):2695-2702, Sep. 1995.
Kaltashov et al., "Advances and challenges in analytical characterization of biotechnology products: Mass spectrometry-based approaches to study properties and behavior of protein therapeutics," Biotechnology Advances., 30:210-222, 2012.
Kaplan et al., "Free light chains in plasma of patients with light chain amyloidosis and non-amyloid light chain deposition disease. High proportion and heterogeneity of disulfide-linked monoclonal free light chains as pathogenic features of amyloid disease," British Journal of Haematology., 144(5):705-715, 2008.
Kaplan et al., "Immunoglobulin free light chain dimers in human diseases," The Scientific World Journal, 11:726-735, Mar. 2011.
Kaplan et al., "Isolation and biochemical characterization of plasma monoclonal free light chains in amyloidosis and multiple myeloma: a pilot study of intact and truncated forms of light chains and their charge properties," Clin. Chem. Lab. Med., 46(3):335-341, Mar. 2008.
Katzmann et al., "Serum reference intervals and diagnostic ranges for free kappa and free lambda immunoglobulin light chains: relative sensitivity for detection of monoclonal light chains," Clin. Chem., 48(9):1437-44, Sep. 2002.
Kohlhagen, "Using MALDI-TOF MS to Screen for Monoclonal Proteins in Serum," The Association for Mass Spectrometry Applications to the Clinical Lab [online] 2015. Retrieved from the Internet: <URL: https://www.msacl.org/2015_US_Long_Abstracts/201412041312 53747.pdf>, MSACL 2015 US: Preliminary Conference Program, San Diego, CA, Mar. 28-Apr. 1, 2015, 2 pages.
Koomen et al., "Proteomic contributions to personalized cancer care," Molecular & Cellular Proteomics, 7.10:1780-1794, 2008.

(56) References Cited

OTHER PUBLICATIONS

Kowarik et al., "The cerebrospinal fluid immunoglobulin transcriptome and proteome in neuromyelitis optica reveals central nervous system-specific B cell populations," J Neuroinflammation., 12:19, Jan. 28, 2015.
Kroon et al., "Identification of sites of degradation in a therapeutic monoclonal antibody by peptide mapping," Pharmaceutical Research., 9:1386-1393, 1992.
Kyle et al., "Criteria for the classification of monoclonal gammopathies, multiple myeloma and related disorders: a report of the International Myeloma Working Group," Br. J. Haematol., 121(5):749-757, Jun. 2003.
Ladwig et al., "Quantification of serum IgG subclasses by use of subclass-specific tryptic peptides and liquid chromatography-tandem mass spectrometry," Clin Chem., 60(8):1080-1088, May 5, 2014.
Landgren et al., "Monoclonal gammopathy of undetermined significance (MGUS) consistently precedes multiple myeloma: a prospective study" Blood, 113(22):5412-5417, May 28, 2009.
Lavatelli et al., "A novel approach for the purification and proteomic analysis of pathogenic immunoglobulin free light chains from serum," Biochimica rt Biophysica Acta., 1814(3):409-419, Mar. 2011.
Lebeau et al., "Generalized crystal-storing histiocytosis associated with monoclonal gammopathy: molecular analysis of a disorder with rapid clinical course and review of the literature," Blood., 100:1817-1827, 2002.
Lefranc, "IMGT, the International ImMunoGeneTics Information System," Cold Spring Harb Protoc., 2011(6):595-603, Jun. 1, 2011.
Leung et al., "A novel and rapid approach to protein expression profiling of cerebrospinal fluid (CSF) from medulloblastoma patients using functionalized magnetic beads, AnchorChipTM technology, MALDI-TOf and MALDI-TOF/TOF mass spectrometry," 33rd Meeting of the Society of Neuroscience, 751.3, Nov. 2003.
Leung et al., "Monoclonal gammopathy of renal significance: when MGUS is no longer undetermined or insignificant," Blood, 120:4292-4295, 2012.
Li et al., "General LC-MS/MS method approach to quantify therapeutic monoclonal antibodies using a common whole antibody internal standard with application to preclinical studies," Analytical Chemistry, 84:1267-1273, 2012.
Li et al., "Simultaneous analysis of multiple monoclonal antibody biotherapeutics by LC-MS/MS method in rat plasma following cassette-dosing," AAPS J., 15(2):337-346, Epub Dec. 12, 2012.
Lindop et al., "Molecular signature of a public clonotypic autoantibody in primary Sjogren's syndrome: A "forbidden" clone in systemic autoimmunity," Arthritis & Rheumatism., 63(11):3477-3486, Oct. 28, 2011.
Liu et al., "Quantitation of a recombinant monoclonal antibody in monkey serum by liquid chromatography-mass spectrometry," Anal Biochem., 414(1):147-153, Epub Mar. 8, 2011.
Lu et al., "Detection of abundant proteins in multiple myeloma cells by proteomics," J Proteomics Bioinform., 3(1):005-009, 2010.
Lu et al., "LC-MS Analysis of Polyclonal Human Anti-Neu5Gc Xeno-Autoantibodies Inmunoglobulin G Subclass and Partial Sequence Using Multistep Intravenous Immunoglobulin Affinity Purification and Multienzymatic Digestion," Analytical Chemistry., 84(6):2761-2768, Mar. 20, 2012.
Marien et al., "Detection of monoclonal proteins in sera by capillary zone electrophoresis and free light chain measurements," Clin. Chem., 48(9):1600-1601, Sep. 2002.
McBride et al., "Chromosomal location of human kappa and lambda immunoglobulin light chain constant region genes," J Exp Med., 155(5):1480-1490, May 1, 1982.
Merlini and Palladini, "Differential diagnosis of monoclonal gammopathy of undetermined significance" Hematology, 595-603, 2012.
Micallef, J. et al, Journal of Hennatology & Oncology 2010, 3, 11 pages.
Minnura et al., "Contrasting glycosylation profiles between Fab and Fc of a human IgG protein studied by electrospray ionization mass spectrometry," J. Immunol. Methods., 326(1-2):116-26, Sep. 2007.
Mohr et al., "High-efficiency nano- and micro-HPLC--high-resolution Orbitrap-MS platform for top-down proteomics," Proteomics., 10(20):3598-3609, Oct. 2010.
Mukhopadhyay et al., "A tribute to Frank Anscombe and random central limit theorem from 1952," Sequential Analysis, 31(3): 265-277, 2012.
Murphy et al., "Characterization of systemic amyloid deposits by mass spectrometry," Methods Enzymol., 412:48-62, 2006.
Murray et al., "Characterization of immunoglobulin by mass spectrometry with applications for the clinical laboratory," Crit. Rev. Clin Lab. Sci., 50(4-5):91-102, Jul.-Oct. 2013.
Nasr et al., "Immunotactoid glomerulopathy: clinicopathologic and proteomic study," Nephrol Dial Transplant., 27(11):4137-4146, Epub Aug. 7, 2012.
Obermeier et al., "Matching of oligoclonal immunoglobulin transcriptomes and proteomes of cerebrospinal fluid in multiple sclerosis," Nat Med., 14(6):688-693, Epub May 18, 2008.
Oeckl et al., "CSF concentrations of cAMP and cGMP are lower in patients with Creutzfeldt-Jakob disease but not Parkinson's disease and amyotrophic lateral sclerosis," PLoS One, 7(3):e32664, Mar. 2012.
Pang et al., "Biomarker discovery in urine by proteomics," Journal of Proteome Research, 1:161-169, Epub Feb. 16, 2002.
Partial Supplementary European Search Report in European Application No. 15/772,546.6, dated Oct. 4, 2017, 16 pages.
Piehler et al., "Quantitation of serum free light chains in combination with protein electrophoresis and clinical information for diagnosing multiple myeloma in a general hospital population," Clin. Chem., 54(11):1823-1830, Nov. 2008.
Radovic, V. V.,"Recommendations for Use of Free Light Chain Assay in Monoclonal Gammopathies" Journal of Medical Biochemistry, 29:1-8, 2010.
Rajkumar et al., "Advances in the diagnosis, classification, risk stratification, and management of monoclonal gammopathy of undertermined significance: implications for recategorizing disease entities in the presence of evolving scientific evidence," Mayo Clinic Proceedings., 85:945-948, 2010.
Remily-Wood et al., "A database of reaction monitoring mass spectrometry assays for elucidating therapeutic response in cancer," Proteomics Clinical Applications, 5:383-396, 2011.
Ren et al., "Reversed-phase liquid chromatography-mass spectrometry of site-specific chemical modifications in intact immunoglobulin molecules and their fragments," J Chromatography A., 1179:198-204, 2008.
Rodriguez et al., "Immunoglobulin derived depositions in the nervous system: novel mass spectrometry application for protein characterization in formalin-fixed tissues," Lab Invest., 88(10):1024-1037, Epub Aug. 18, 2008.
Rosati et al., "Exploring an orbitrap analyzer for the characterization of intact antibodies by native mass spectrometry," Angew. Chem. Int. Ed. Engl., 51(52):12992-12996, Dec. 2012.
Ruan et al., "Strategy and its implications of protein bioanalysis utilizing high-resolution mass spectrometric detection of intact protein," Anal. Chem., 83(23):8937-8944, Dec. 2011.
Schaefer et al., "Residual serum monoclonal protein predicts progression-free survival in patients with previously untreated multiple myeloma," Cancer., 116:640-646, 2010.
Sethi et al., "Mass spectrometry-based proteomic diagnosis of renal immunoglobulin heavy chain amyloidosis," Clin J Am Soc Nephrol., 5:2180-2187, 2010.
Singh et al., "Cerebrospinal-fluid-derived immunoglobulin G of different multiple sclerosis patients shares mutated sequences in complementarity determining regions," Mol Cell Proteomics, 12(12):3924-3934, Epub Aug. 22, 2013.
Song et al., "Characterization of N-terminal processing of group VIA phospholipase A2 and of potential cleavage sites of amyloid precursor protein constructs by automated identification of signature peptides in LC/MS/MS analyses of proteolytic digests," J Am Soc Mass Spectrom., 15(12):1780-1793, Dec. 2004.

(56) References Cited

OTHER PUBLICATIONS

Stoop et al., "Quantitative MALDI-FT-ICR analysis of cerebrospinal fluid of relapsing-remitting and primary progressive multiple sclerosis patients," Multiple Sclerosis., 15(9):S83, Sep. 2009.

Stubbs et al., "Anti-neurofilament antibodies in neuropathy with monoclonal gammopathy of undetermined significance produce experimental motor nerve conduction block," Acta Neuropathology., 105:109-116, 2003.

Sun et al., "Immunoglobulin genes and diversity: what we have learned from domestic animals," J Anim Sci Biotechnol., 3(1):18, Jun. 20, 2012.

Theis et al., "Immunoglobulin Light Chain Gene Constant Region is an Invariable Part of Amyloid Deposits in AL Amyloidosis," Blood, 112(11):3128, Nov. 16, 2008.

Theis et al., "Mass spectrometry based proteomic analysis of AL amyloidosis: Immunoglobulin Light Chain Gene Constant Region is an Invariable Part of Amyloid Deposits and provides valuable diagnostic target," presented at the United States and Canadian Academy of Pathology Annual Meeting, Mar. 2009, 1 page.

Thermo Scientific, "MelonTM Gel IgG Spin Purification Kit" [online], 2011 [retrieved on Aug. 6, 2011]. Retrieved from the Internet: <URL: https://tools.lifetechnologies.com/content/sfs/manuals/MAN0011513_Melon_Gel_1gG_Spin_Purifi_UG.pdf, 4 pages.

Thurgood et al., "An Immunodominant La/SSB autoantibody proteome derives from public clonotypes," Clinical and Experimental Immunology., 174:237-244, Oct. 6, 2013.

VanDuijn et al., "Immune responses are characterized by specific shared immunoglobulin peptides that can be detected by proteomic techniques," Journal of Biological Chemistry, 285:29247-29253, Jul. 8, 2010.

Verheesen et al., "Beneficial properties of single-domain antibody fragments for application in immunoaffinity purification and immunoperfusion chromatography," Biochim Biophys Acta., 1624(1-3):21-28, Dec. 5, 2003.

Vrana et al., "Amyloidosis typing based on Laser Microdissection and Mass Spectrometry of Paraffin-Embedded Tissue Biopsies" Companion to Peripheral Neuropathy, pp. 347-349, 2010.

Vrana et al., "Classification of Amyloidosis in Fat Aspiration Specimens Using Mass Spectrometry Based Proteomics," presented at the United States and Canadian Academy of Pathology Annual Meeting, Mar. 2009, 1 page.

Vrana et al., "Diagnosis and Classification of Amyloidosis in Abdominal Subcutaneous Fat Aspiration Specimens Using Mass Spectrometry Based Proteomics," Blood, 112(11):2710, Nov. 16, 2008.

Vrana et al., "Diagnosis and Typing of Cardiac Amyloidosis in Routine Clinical Specimens by Mass Spectrometry Based Proteomic Analysis," presented at the United States and Canadian Academy of Pathology Annual Meeting, Mar. 2009, 1 page.

Wang et al., "Construction of a Multiple Myeloma Diagnostic Model by Magnetic Bead-Based MALDI-TOF Mass Spectrometry of Serum and Pattern Recognition Software" Anatomical Record, 292:604-610, 2009.

Wang et al., "Differentiation and quantification of endogenous and recombinant-methionyl human leptin in clinical plasma samples by immunocapture/mass spectrometry," J. Pharm. Biomed. Anal., 70:440-446, Nov. 2012.

Whiteaker et al., "Sequential multiplexed analyte quantification using peptide immunoaffinity enrichment coupled to mass spectrometry," Mol Cell Proteomics., 11(6):10.1074/mcp.M111.015347, 2012,10 pages.

Willrich et al., "Quantitation of infliximab using clonotypic peptides and selective reaction monitoring by LC-MS/MS," International Immunopharmacology., 28(1): 513-520, Sep. 1, 2015.

Willrich et al., "Serum infliximab quantitation by LC-MS/MS in patients treated for inflammatory disorders," Gastroenterology AGA Abstracts., Sa1252, May 1, 2014, Retrieved from the internet: URL:https://ac.els-cdn.com/S0016508514608568/1-S2.0-S0016508514608568-main.pdf?_tid=e58e3b4c-ca0a-11e7-96b2-00000aab0f6b&acdnat=1510753563_74ab7a6b0b5f976b8c948a995d894fce, Retrieved on Nov. 15, 2017, Abstract Only.

Zhang et al., "Characterization of variable regions of monoclonal antibodies by top-down mass spectrometry," Anal Chem., 79(15):5723-5729, 2007.

Zhaoyu et al., "Alteration of DBP levels in CSF of patients with MS by proteomics analysis," Cell Mol. Neurobiol., 29(2):203-210, Mar. 2009.

Kappa Light Chain Constant Region Amino Acid Sequence

TVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

105 Amino Acids
Average Molecular Mass: 11608.86 Da

Lambda Light Chain Constant Region Amino Acid Sequences: L1, L2, L3 and L7

L1  QPKA#PSVTLFPPSSEELQANKATLVCLISDFYPGAVTVAWKADGSPVKAGVETTKPSKQSNNKYAASSYLSLTPEQWKSHRSYSCQVTHEGSTVEKTVAPTECS
L2  QPKAAPSVTLFPPSSEELQANKATLVCLISDFYPGAVTVAWKAD#SPVKAGVETTPSKQSNNKYAASSYLSLTPEQWKSHRSYSCQVTHEGSTVEKTVAPTECS
L3  QPKAAPSVTLFPPSSEELQANKATLVCLISDFYPGAVTVAWKAD#SPVKAGVETTPSKQSNNKYAASSYLSLTPEQWKSH#SYSCQVTHEGSTVEKTVAPTECS
L7  QPKAAPSVTLFPPSSEELQANKATLVCL#SDFYPGAVTVAWKADGSP##GVETTKPSKQSNNKYAASSYLSLTPEQWKSHRSYSC#VTHEGSTVEKTVAPT#ECS

105 Amino Acids
L1 Average Molecular Mass: 11290.61 Da
L2 Average Molecular Mass: 11236.52 Da
L3 Average Molecular Mass: 11208.50 Da
L4 Average Molecular Mass: 11245.62 Da Average Molecular Mass = 11,245.31

Mass Difference between Kappa and Lambda Constant Regions= 363.55 Da

FIG. 2

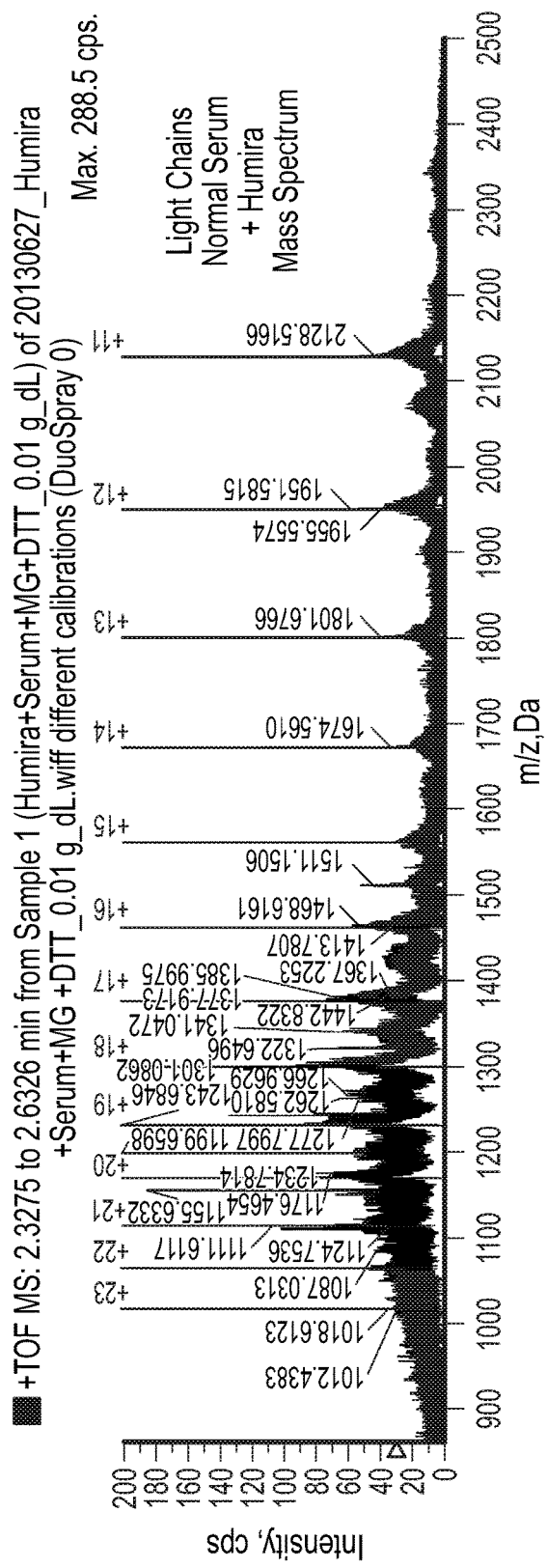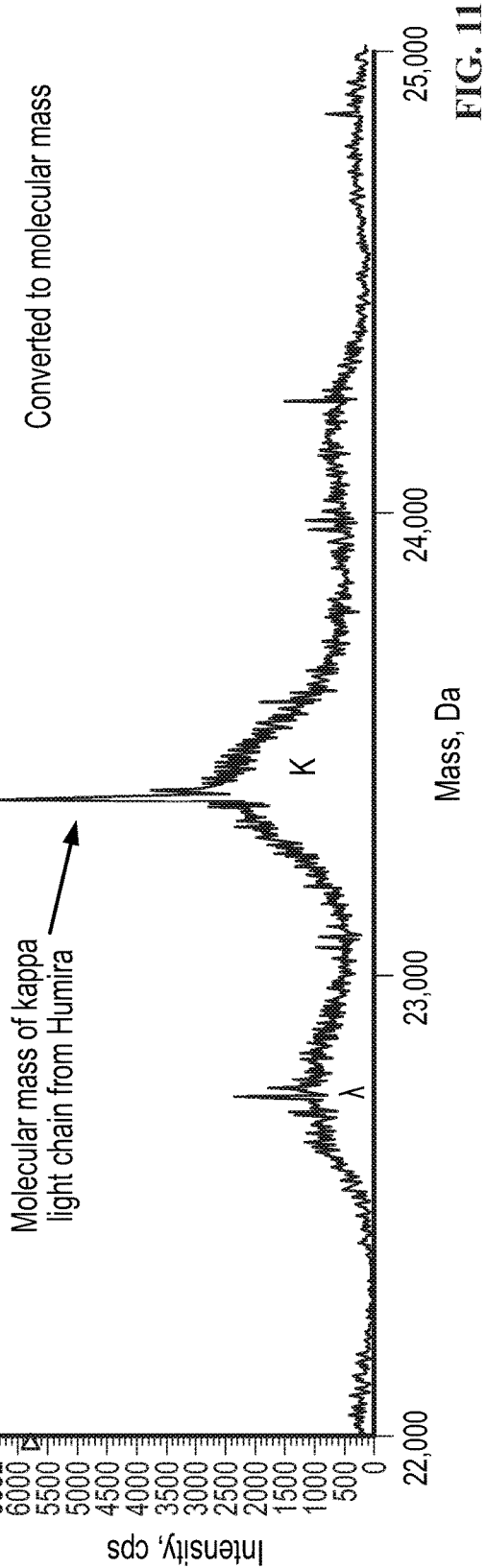
FIG. 11

ISOTYPING IMMUNOGLOBULINS USING ACCURATE MOLECULAR MASS

CROSS-REFERENCE

This application is a continuation of U.S. application Ser. No. 15/301,633, filed Oct. 3, 2016 (now U.S. Pat. No. 10,267,806), which is a National Stage Application under 35 U.S.C. § 371 of International Application No. PCT/US2015/024379, filed Apr. 3, 2015, which claims the benefit of U.S. Provisional Application No. 61/975,524, filed Apr. 4, 2014, which are hereby incorporated by reference in their entirety.

SEQUENCE LISTING

The instant application contains a Sequence Listing which has been submitted to the United States Patent and Trademark Office via the electronic filing system. The ASCII text file, which is incorporated-by-reference herein, was created on Sep. 4, 2019, is named 07039_1328002_ST25.txt, and is 5,270 bytes in size.

TECHNICAL FIELD

This document relates to methods for detecting and quantifying heavy and light chains of immunoglobulin using mass spectrometry techniques.

BACKGROUND

Human immunoglobulins contain two identical heavy chain polypeptides (each about 54 kilodaltons in MW) and two identical light chain polypeptides (each about 24 kilodaltons in molecular weight) which are bound together by disulfide bonds. Each light chain and each heavy chain include a constant region and a variable region. The variable region is located on the N-terminal portion of each chain and the constant region is located on the C-terminal portion of each chain. The constant regions of the light chains and heavy chains have different amino acid sequences, and can be used to identify the isotype of the heavy or light chain. In humans, there are two different isotypes of light chain polypeptides referred to as either kappa or lambda; and five different isotypes of heavy chain polypeptides referred to as gamma (IgG), alpha (IgA), mu (IgM), epsilon (IgE), and delta (IgD).

Clinical laboratories currently quantify and isotype serum immunoglobulins using a combination of protein gel electrophoresis (PEL) and imunogixation (IFE). For a normal healthy individual the electrophoretic pattern observed is an evenly dispersed staining pattern. This pattern reflects the polyclonal background produced by the large number (approximately $6.3 \times 10^6$ heavy chains and $3.5 \times 10^5$ light chains) of immunoglobulin heavy chains and light chains generated as a function of somatic hypermutation. In certain diseases, such as polyclonal gammopathy, there is an increase in the total amount of immunoglobulins in the bloodstream or in urine relative to a healthy individual. In other diseases, such as multiple myeloma, this increase in the amount immunoglobulins is due to a monoclonal immunoglobulin in the bloodstream. If high levels of the monoclonal immunoglobulin are detected, additional tests are performed to determine the isotypes of the heavy and light chains of the monoclonal immunoglobulin.

Likewise, clinical laboratories now assess cerebral spinal fluid (CSF) with isoelectric focusing gel electrophoresis followed by IgG immunoblotting (IgG IEF) to detect IgG clones in CSF as compared to serum. See e.g., Fortini A S, Sanders E L, Weinshenker B G, Katzmann J A. *Am J Clin Pathol*. 2003 November; 120(5):672-5. One or more CSF bands (i.e. oligoclonal bands; OCB) that are not present in serum suggest that B cell clones are actively producing IgG as part of an inflammatory response in the CNS. Detection of OCB is a sensitive method for CSF inflammatory diseases, and in MS 95% of patients have IgG CSF-specific OCB. Awad A, Hemmer B, Hartung H P, Kieseier B, Bennett J L, Stuve O. *J Neuroimmunol*. 2010 Feb. 26; 219(1-2):1-7.

SUMMARY

Provided herein are methods of detecting immunoglobulin light chains, immunoglobulin heavy chains, or mixtures thereof in a sample. The method includes providing a sample comprising an immunoglobulin light chain, an immunoglobulin heavy chain, or mixtures thereof; immunopurifying, diluting, and/or concentrating the sample; and subjecting the sample to a mass spectrometry technique to obtain a mass spectrum of the sample.

In some embodiments, the immunopurifying includes using an antibody selected from the group consisting of an anti-human IgG antibody, an anti-human IgA antibody, an anti-human IgM antibody, an anti-human IgD antibody, an anti-human IgE antibody, an anti-human kappa antibody, an anti-human lambda antibody, and combinations thereof. The antibody can be a non-human antibody. In some embodiments, the non-human antibody is at least one of a camelid antibody, a cartilaginous fish antibody, llama, sheep, goat, or a mouse antibody.

In some embodiments, the antibody for immunopurification is a single domain antibody fragment. The single domain antibody fragment (SDAF) can be selected from the group consisting of an anti-human IgG SDAF, an anti-human IgA SDAF, an anti-human IgM SDAF, an anti-human IgD SDAF, an anti-human IgE SDAF, an anti-human kappa SDAF, an anti-human lambda SDAF, and combinations thereof. In some embodiments, the single domain antibody fragment is derived from a camelid antibody, a cartilaginous fish antibody, llama, a mouse antibody, sheep, goat, or a human antibody.

The single domain antibody fragment can be selected such that the mass spectrum generated in step c) for the single domain antibody fragment does not overlap with the mass spectrum generated in step c) for the immunoglobulin light chain or immunoglobulin heavy chain. In some embodiments, the single domain antibody fragment is selected such that the single domain antibody fragment generates a signal of about 12,500 to about 15,000 m/z in step c) with a single charge.

In some embodiments, the immunoglobulin light chains are decoupled from the immunoglobulin heavy chains prior to subjecting the sample to a mass spectrometry technique to obtain a mass spectrum of the sample. The immunoglobulin light chains can be decoupled by cleavage of the disulfide bonds between the light and heavy chains. For example, the disulfide bonds can be cleaved using a reducing agent capable of reducing the disulfide bonds. In some embodiments, the reducing agent is selected from the group consisting of DTT (2,3 dihydroxybutane-1,4-dithiol), DTE (2,3 dihydroxybutane-1,4-dithiol), thioglycolate, cysteine, sulfites, bisulfites, sulfides, bisulfides, TCEP (tris(2-carboxyethyl)phosphine), and salt forms thereof.

In some embodiments, the method further includes determining the ratio of kappa and lambda immunoglobulin light chains in the sample after step subjecting the sample to a mass spectrometry technique to obtain a mass spectrum of the sample.

In some embodiments, the light chains are not fragmented during the mass spectrometry technique.

The sample can be a biological sample. For example, the biological sample can be a whole blood sample, a serum sample, a plasma sample, a urine sample, or a cerebral spinal fluid sample. The biological sample can be a mammalian biological sample. In some embodiments, the mammalian biological sample is a human biological sample.

In some embodiments, the mass spectrometry technique includes a liquid chromatography-mass spectrometry (LC-MS) technique. For example, the mass spectrometry technique can include a microflow liquid chromatography electrospray ionization coupled to a quadrupole time-of-flight mass spectrometry (microLC-ESI-Q-TOF MS) technique. In some embodiments, the LC-MS technique includes the use of positive ion mode.

In some embodiments, the mass spectrometry technique includes a matrix assisted laser adsorption ionization-time of flight mass spectrometry (MALDI-TOF MS) technique.

In some embodiments, the sample including immunoglobulin light chains, immunoglobulin heavy chains, or mixtures thereof is analyzed as a single fraction in a single analysis.

The method can further include determining the pairing of immunoglobulin heavy chains and immunoglobulin light chains in the sample. In some embodiments, the method further includes isotyping one or more of the immunoglobulin light chains in the sample. In some embodiments, the method further includes isotyping one or more of the immunoglobulin heavy chains in the sample. In some embodiments, the method further includes isotyping one or more of the immunoglobulin light chains and immunoglobulin heavy chains in the sample. In some embodiments, the method further includes identifying one or more of the immunoglobulin light chains and immunoglobulin heavy chains. In some embodiments, the method further includes quantitating the amount of one or more of the immunoglobulin light chains and immunoglobulin heavy chains in the sample.

In some embodiments, the method further includes identifying the M-protein in the sample. The method can further include quantifying the M-protein in the sample. In some embodiments, the method further includes identifying determining the pairing of immunoglobulin heavy chains and immunoglobulin light chains in the M-protein in the sample.

In some embodiments, the ratio of the kappa and lambda light chains is determined by measuring the peak area of one or more multiply charged ion peaks corresponding to each chain. The kappa and lambda light chains can be quantified by converting the peak area of the multiply charged ion peaks to a molecular mass. In some embodiments, a surrogate internal standard can be used such that the mass of the internal standard dose not overlap with the mass of the protein being quantitated.

Accordingly, provided herein is a method for detecting immunoglobulin light chains, immunoglobulin heavy chains, or mixtures thereof in a sample. The method includes (a) providing a sample comprising an immunoglobulin light chain, an immunoglobulin heavy chain, or mixtures thereof; (b) immunopurifying the sample utilizing a single domain antibody fragment; (c) decoupling light chain immunoglobulins from heavy chain immunoglobulins; and (d) subjecting the immunopurified sample to a mass spectrometry technique to obtain a mass spectrum of the sample; (e) determining one or more of (i) the ratio of kappa and lambda immunoglobulin light chains; (ii) the isotype of the immunoglobulin light chains; (iii) the isotype of the immunoglobulin heavy chains; (iv) the isotype of one or more of the immunoglobulin light chains and immunoglobulin heavy chains; and (v) the quantitative amount of one or more of the immunoglobulin light chains and immunoglobulin heavy chains in the sample. The mass spectrometry technique is chosen from the group consisting of (i) liquid chromatography electrospray ionization coupled to mass analyzer (quadrupole, time of flight or orbitrap) (ii) a microflow liquid chromatography electrospray ionization coupled to a quadrupole time-of-flight mass spectrometry (microLC-ESI-Q-TOF MS or MS/MS) technique and (iii) a matrix assisted laser adsorption ionization-time of flight mass spectrometry (MALDI-TOF MS or MS/MS) technique.

Also, provided herein is a method for analyzing immunoglobulin light chains, immunoglobulin heavy chains, or mixtures thereof in a sample. The method includes (a) providing a sample comprising an immunoglobulin light chain, an immunoglobulin heavy chain, or mixtures thereof; (b) immunopurifying the sample utilizing a single domain antibody fragment; (c) optionally decoupling the light chain immunoglobulins from the heavy chain immunoglobulins, wherein one or more of the immunoglobulin light chains or immunoglobulin heavy chains are derived from an M-protein; (d) subjecting the immunopurified sample to a mass spectrometry technique to obtain a mass spectrum of the sample; and (e) determining one or more of (i) the identity of the M-protein; (ii) the quantity of the M-protein; (iii) the pairing of immunoglobulin heavy chains and immunoglobulin light chains of the M-protein; and (iv) the quantitative amount of one or more of the immunoglobulin light chains, immunoglobulin heavy chains, and M-protein in the sample. The mass spectrometry technique is chosen from the group consisting of (i) liquid chromatography electrospray ionization coupled to mass analyzer (quadrupole, time of flight or orbitrap) (ii) a microflow liquid chromatography electrospray ionization coupled to a quadrupole time-of-flight mass spectrometry (microLC-ESI-Q-TOF MS or MS/MS) technique and (iii) a matrix assisted laser adsorption ionization-time of flight mass spectrometry (MALDI-TOF MS or MS/MS) technique. Further, provided herein is a method for diagnosing a disorder in a subject. The method includes providing a sample from the subject comprising an immunoglobulin light chain, an immunoglobulin heavy chain, or mixtures thereof; immunopurifying the sample; subjecting the immunopurified sample to a mass spectrometry technique to obtain a mass spectrum of the sample; determining the ratio of the kappa and lambda immunoglobulin light chains in the sample; and comparing the ratio to a reference value.

The disorder can be selected from the group consisting of an autoimmune disorder, an inflammatory disorder, an infectious disorder, and a polyclonal gammopathy. In some embodiments, the disorder is selected from the group consisting of plasma cell dyscrasias, hypergammaglobulinemia, multiple sclerosis, neuromyelitus optica, neurosarcoidosis, subacute sclerosing panencephalitis, ANCA associated vasculitis, paraneoplastic syndromes, celiac disease, Sjogrens Syndrome, rheumatoid arthritis, and Guillian-Barrre Syndrome. ANCA associated vasculitis includes three systemic autoimmune small vessel vasculitis syndromes that are associated with antineutrophil cytoplasmic autoantibodies (ANCAs). ANCA associated vasculitis includes microscopic polyangiitis (MPA), granulomatosis with polyangiitis (GPA), formerly known as Wegener's granulomatosis, and eosinophilic granulomatosis with polyangiitis (EGPA), formerly known as Churg-Strauss syndrome. When the disorder is hypergammaglobulinemia, in addition to the kappa and lambda ratio, distinct monoclonal light chains can be identified above the polyclonal background. The method can be performed to confirm the results of a protein electrophoresis (PEL) or immunofixation test.

Additionally, provided herein is a method of monitoring a treatment of a disorder in a subject, wherein the disorder is associated with an abnormal kappa and lambda immunoglobulin light chain ratio. The method includes (a) providing an initial sample from the subject; (b) providing one or more secondary samples from the subject during the treatment, after the treatment, or both; (c) immunopurifying the sample; (d) subjecting the samples to a mass spectrometry technique to obtain a mass spectrum of the sample; (e) determining the ratio of the kappa and lambda immunoglobulin light chains in the samples; and (f) comparing the ratios from the initial and the one or more secondary samples.

Further, provided herein is a method for quantifying the kappa and lambda immunoglobulin light chains in a sample. The method includes (a) providing a sample comprising one or more immunoglobulin light chains; (b) immunopurifying the samples; (c) subjecting the immunopurified sample to a mass spectrometry technique to obtain a mass spectrum of the samples; (d) identifying the multiply charged ion peaks in the spectrum corresponding to the kappa and lambda immunoglobulin light chains; and (e) converting the peak area of the identified peaks to a molecular mass to quantify the kappa and lambda immunoglobulin light chains in the sample.

Provided herein is a method of diagnosing a disorder in a subject, wherein the disorder is associated with an inflammatory response in the central nervous system. The method includes (a) providing a cerebral spinal fluid (CSF) sample comprising one or more immunoglobulins; (b) subjecting the CSF sample to a mass spectrometry technique to obtain a mass spectrum of the CSF sample; and (c) identifying a mass peak corresponding to one or more immunoglobulin light chains in the CSF sample.

In some embodiments, the immunoglobulin light chains are decoupled by cleavage of the disulfide bonds between the light and heavy chains. The disulfide bonds can be cleaved using a reducing agent capable of reducing the disulfide bonds. For example, the reducing agent can be selected from the group consisting of: DTT (2,3 dihydroxybutane-1,4-dithiol), DTE (2,3 dihydroxybutane-1,4-dithiol), thioglycolate, cysteine, sulfites, bisulfites, sulfides, bisulfides, TCEP (tris(2-carboxyethyl)phosphine), and salt forms thereof.

In some embodiments, prior to subjecting the CSF sample to a mass spectrometry technique to obtain a mass spectrum of the CSF sample, the CSF sample is diluted. For example, the CSF sample can be diluted with buffer.

In some embodiments, the mass spectrometry technique includes a liquid chromatography-mass spectrometry (LC-MS) technique. The mass spectrometry technique can include a microflow liquid chromatography electrospray ionization coupled to a quadrupole time-of-flight mass spectrometry (microLC-ESI-Q-TOF MS/MS) technique. The LC-MS technique can include the use of positive ion mode.

In some embodiments, the disorder is selected from the group consisting of plasma cell dyscrasias, hypergammaglobulinemia, multiple sclerosis, neuromyelitus optica, neurosarcoidosis, subacute sclerosing panencephalitis, ANCA associated vasculitis, paraneoplastic syndromes, celiac disease, Sjogrens Syndrome, rheumatoid arthritis, and Guillian-Barrre Syndrome The method can further include providing a serum sample including one or more immunoglobulins, subjecting the serum sample to a mass spectrometry technique to obtain a mass spectrum of the sample; identifying a mass peak corresponding to one or more light chains in the serum sample; and comparing (i) the mass peaks corresponding to the one or more light chains in the CSF sample to (ii) the mass peaks corresponding to one or more light chains in the serum sample.

In some embodiments, the serum sample is enriched prior to subjecting the sample to the mass spectrometry technique.

The presence of one or more peaks in the CSF sample not present in the serum sample can indicate an inflammatory response in the central nervous system. For example, the one or more peaks in the CSF sample not present in the serum sample can include an oligoclonal band (OCB).

Accordingly, provided herein is a method of diagnosing a disorder in a subject, wherein the disorder is associated with an inflammatory response in the central nervous system. The method includes (a) providing a CSF sample comprising one or more immunoglobulins and a serum sample comprising one or more immunoglobulins; (b) subjecting the CSF sample and the serum sample to a mass spectrometry technique to obtain a mass spectrum of the CSF sample and serum sample; (c) identifying a mass peak corresponding to one or more light chains in the CSF sample; (e) identifying a mass peak corresponding to one or more light chains in the serum sample; and (f) comparing (i) the mass peaks corresponding to the one or more light chains in the CSF sample to (ii) the mass peaks corresponding to one or more light chains in the serum sample.

Also provided herein is a method for monitoring a response to a treatment. The method includes (a) providing an initial CSF sample from the subject; (b) providing one or more secondary CSF samples from the subject during the treatment, after the treatment, or both; (c) immunopurifying the CSF samples; (d) subjecting the immunopurified CSF samples to a mass spectrometry technique to obtain a mass spectrum of the CSF samples; (e) comparing (i) the mass peaks in the initial CSF sample to (ii) the mass peaks in the one or more secondary samples. The initial sample can be a baseline sample or a control sample, or, for example a sample taken from the subject prior to the start of treatment.

Also provided herein are methods of using mass spectrometry methods (e.g., microLC-ESI-Q-TOF MS) for identifying and quantifying the heavy and light chains of immunoglobulins in biological samples. This is due, in part, to the fact that the mass difference of the constant regions of various isotypes of both the heavy and light chains contribute to the observation of distinct molecular mass profiles for each isotype. Using immunoglobulin enriched, DTT reduced, pooled normal human serum as a reference, molecular mass profiles for each isotype were established and found to fit a normal distribution. Moreover, in the case of the immunoglobulin light chains, the kappa/lambda peak area ratios are analogous to the kappa/lambda ratios observed using other published methods. In addition, the methods provided herein can be used to monitor kappa and lambda light chain repertoires in serum (e.g., in various mammalian species). The results shown for subjects with hypergammaglobulinemia and other disorders further highlight the usefulness of the methods provided herein for assessing the relative abundance of the kappa and lambda light chain repertoires in subjects with abnormal immunoglobulin levels. This finding is significant since it demonstrates that an abnormal polyclonal kappa/lambda ratio in serum can be identified quickly and inexpensively using the molecular mass profiling methods described herein. In addition, detection and isotyping the immunoglobulin heavy chains can have implications in the identification and treatment of disorders such as Multiple Myeloma.

Accordingly, provided herein is a method for determining a ratio of kappa and lambda immunoglobulin light chains in a sample, the method comprising: providing a sample comprising one or more immunoglobulin light chains; subjecting the sample to a mass spectrometry technique to obtain a mass spectrum of the sample; and determining the ratio of the kappa and lambda immunoglobulin light chains in the sample.

In some embodiments, the immunoglobulin light chains are decoupled from the immunoglobulin heavy chains prior to subjecting the sample to a mass spectrometry technique. For example, the immunoglobulin light chains can be decoupled by cleavage (e.g., reduction) of the disulfide bonds between the light and heavy chains. Any suitable reducing agent can be used, for example, the reducing agent can be selected from the group consisting of: DTT (2,3 dihydroxybutane-1,4-dithiol), DTE (2,3 dihydroxybutane-1, 4-dithiol), thioglycolate, cysteine, sulfites, bisulfites, sulfides, bisulfides, TCEP (tris(2-carboxyethyl)phosphine), and salt forms thereof. In some embodiments, the immunoglobulins in the sample are enriched in the sample prior to subjecting the sample to a mass spectrometry technique.

In some embodiments, the light chains are not fragmented during the mass spectrometry technique.

A sample can include a biological sample such as a whole blood sample, serum sample, plasma sample, or urine sample. In some embodiments, the biological sample is a mammalian biological sample (e.g., a human biological sample).

The mass spectrometry techniques used herein can include a liquid chromatography-mass spectrometry (LC-MS) technique. In some embodiments, the mass spectrometry technique comprises a microflow liquid chromatography electrospray ionization coupled to a quadrupole time-of-flight mass spectrometry (microLC-ESI-Q-TOF MS) technique. In some embodiments, the LC-MS technique comprises the use of positive ion mode.

In some cases, the ratio of the kappa and lambda light chains is determined by measuring the peak area of one or more multiply charged ion peaks corresponding to each chain. The peak areas of the multiply charged ion peaks can be converted to a molecular mass. In some embodiments, the molecular mass measurements can be used to quantify the kappa and lambda light chains.

In some embodiments, a method for determining a ratio of kappa and lambda immunoglobulin light chains in a sample comprises: providing a sample enriched in one or more immunoglobulins; decoupling light chain immunoglobulins from heavy chain immunoglobulins in the immunoglobulins in the sample to generate a decoupled immunoglobulin sample; subjecting the sample to a microflow liquid chromatography electrospray ionization coupled to a quadrupole time-of-flight mass spectrometry technique to obtain a mass spectrum of the sample; and determining the ratio of the kappa and lambda immunoglobulin light chains in the sample.

Also provided herein is a method for diagnosing a disorder in a subject, the method comprising: providing a sample from the subject comprising one or more immunoglobulin light chains; subjecting the sample to a mass spectrometry technique to obtain a mass spectrum of the sample; determining the ratio of the kappa and lambda immunoglobulin light chains in the sample; and comparing the ratio to a reference value. Exemplary disorders that can be diagnosed using these methods include an autoimmune disorder, an inflammatory disorder, an infectious disorder, and a polyclonal gammopathy. In some embodiments, the disorder is hypergammaglobulinemia and in addition to the kappa and lambda ratio, distinct monoclonal light chains can be identified above the polyclonal background. In some embodiments, the methods described herein are performed to confirm the results of a protein electrophoresis (PEL) or immunofixation test.

Further provided herein is a method of monitoring a treatment of a disorder in a subject, wherein the disorder is associated with an abnormal kappa and lambda immunoglobulin light chain ratio, the method comprising: providing a first sample of the subject before the treatment; providing a second sample of the subject during or after the treatment; subjecting the samples to a mass spectrometry technique to obtain a mass spectrum of the sample; determining the ratio of the kappa and lambda immunoglobulin light chains in the samples; and comparing the ratios from the first and second samples.

The methods provided herein can also be used to quantifying the kappa and lambda immunoglobulin light chains in a sample. In some embodiments, the method comprises: providing a sample comprising one or more immunoglobulin light chains; subjecting the sample to a mass spectrometry technique to obtain a mass spectrum of the sample; identifying the multiply charged ion peaks in the spectrum corresponding to the kappa and lambda immunoglobulin light chains; and converting the peak area of the identified peaks to a molecular mass to quantify the kappa and lambda immunoglobulin light chains in the sample.

Provided herein is a method for diagnosing hypergammaglobulinemia in a subject, the method comprising: providing a sample from the subject comprising one or more immunoglobulin light chains; subjecting the sample to a mass spectrometry technique to obtain a mass spectrum of the sample; determining the total amount of the kappa and lambda immunoglobulin light chains in the sample; and comparing the amount in the sample to a reference value, wherein a higher than reference total amount indicates that the subject has hypergammaglobulinemia. In some embodiments, the total amount of the kappa and lambda immunoglobulin light chains in the sample is at least 2-fold higher than the reference value.

The methods described herein are also useful for determining the isotype of one or more immunoglobulin heavy chains in a sample. In some embodiments, the method comprises: providing a sample comprising one or more immunoglobulin heavy chains; subjecting the sample to a mass spectrometry technique to obtain a mass spectrum of the sample; and identifying the mass peaks corresponding to one or more isotypes of an immunoglobulin heavy chain in the sample.

Also provided herein is a method for determining the isotype of one or more immunoglobulin light chains in a sample, the method comprising: providing a sample comprising one or more immunoglobulin light chains; subjecting the sample to a mass spectrometry technique to obtain a mass spectrum of the sample; and identifying the mass peaks corresponding to one or more isotypes of an immunoglobulin light chain in the sample.

The method provided herein can be used to diagnose a disorder in a subject, wherein the disorder is associated with one or more heavy chain immunoglobulin isotypes, the method comprising: providing a sample comprising one or more immunoglobulin heavy chains; subjecting the sample to a mass spectrometry technique to obtain a mass spectrum of the sample; and identifying the mass peaks corresponding to one or more isotypes of an immunoglobulin heavy chain in the sample. Exemplary disorders include monoclonal gammopathy of underdetermined significance (MGUS), light chain deposition disease, amyloidosis, multiple myeloma, heavy chain deposition disease, and POEMS syndrome.

Unless otherwise defined, all technical and scientific terms used herein have the same meaning as commonly understood by one of ordinary skill in the art to which this description belongs. Methods and materials are described herein for use in the present invention; other, suitable methods and materials known in the art can also be used. The materials, methods, and examples are illustrative only and not intended to be limiting. All publications, patent applications, patents, and other references mentioned herein are incorporated by reference in their entirety. In case of conflict, the present specification, including definitions, will control. Other features and advantages of the invention will be apparent from the following detailed description and figures, and from the claims.

DESCRIPTION OF DRAWINGS

FIG. 2 shows the amino acid sequences for the constant regions for kappa (SEQ ID NO:1) and lambda light chains (L1: SEQ ID NO:2; L2: SEQ ID NO:3; L3: SEQ ID NO:4; and L7: SEQ ID NO:5) along with the molecular mass difference between the kappa constant region and the average mass of the four lambda constant regions.

FIG. 11 shows the response observed in the light chain mass region for a serum sample spiked with the monoclonal recombinant therapeutic antibody HUMIRA® (adalimumab) which has a kappa light chain and an IgG heavy chain.

DETAILED DESCRIPTION

The amino acid sequence of a human immunoglobulin light chain consists of three regions: the N-terminal V region (approximately 107 amino acids for kappa and 110 amino acids for lambda), the J region (12 amino acids), and the C-terminal C region (106 amino acids). Each region is translated from a specific set of genes expressed only in B cells which make and secrete light chains either as part of an intact immunoglobulin or as a free light chain. B-cells are also able to randomly mutate V and J region genes for light chains through the process of somatic hypermutation resulting in a large number of different gene combinations (approximately $1.3 \times 10^3$ for kappa alone) (see, e.g., Lefranc, M P. *Cold Spring Harb Protoc* 2011; 2011:595-603). Since the light chain V and J region gene sequences are created randomly, the Central Limit Theorem (Mukhopadhyay, N and Chattopadhyay, B. *Sequential Anal* 2012; 31:265-77) predicts that the amino acid sequence of the expressed light chain repertoire should have a normally distributed molecular mass profile.

Figure 1:
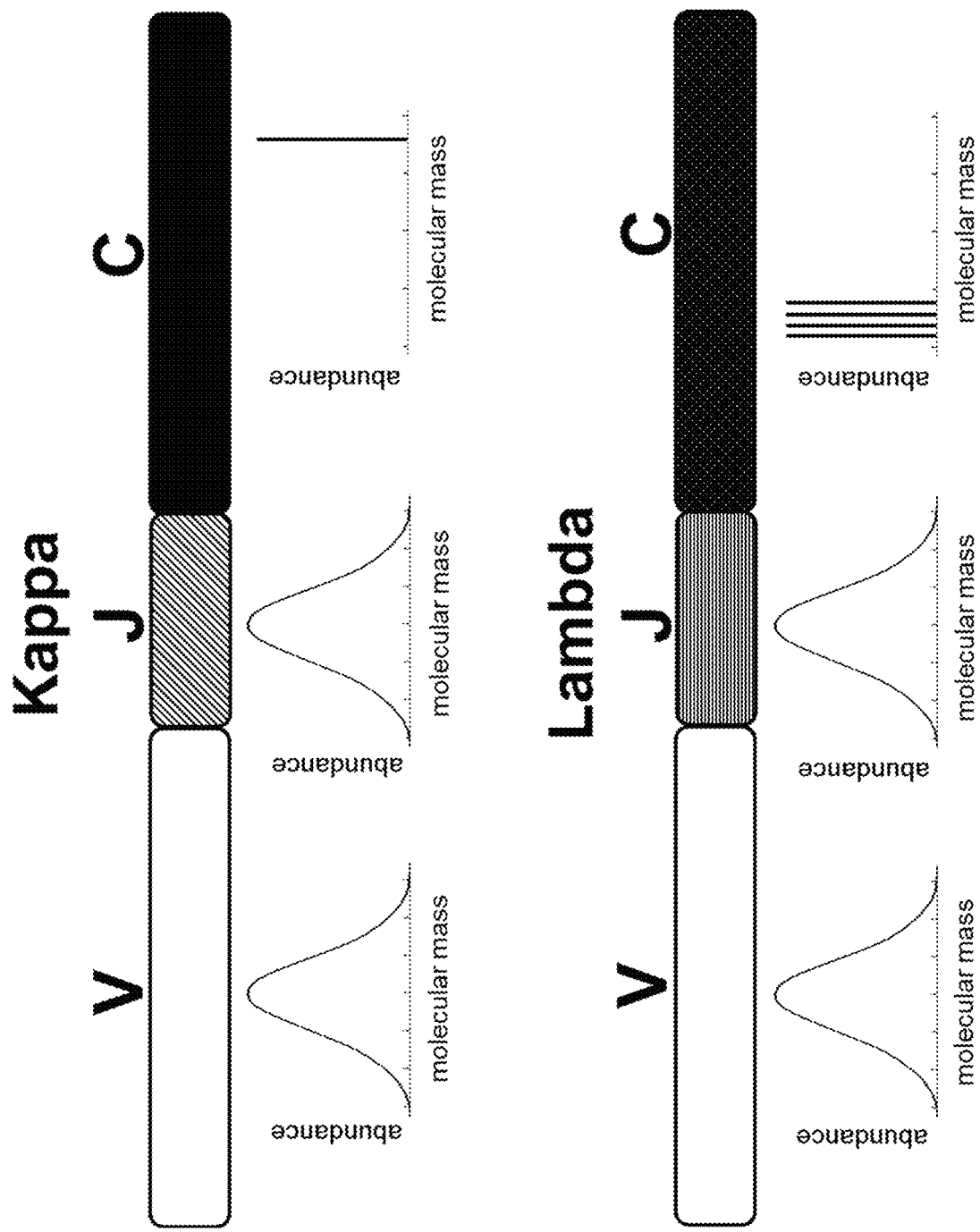
FIG. 1 illustrates the expected theoretical molecular mass profiles that would be observed for each of the three regions (V, J, and C) for both kappa and lambda light chains.
Figure 3:
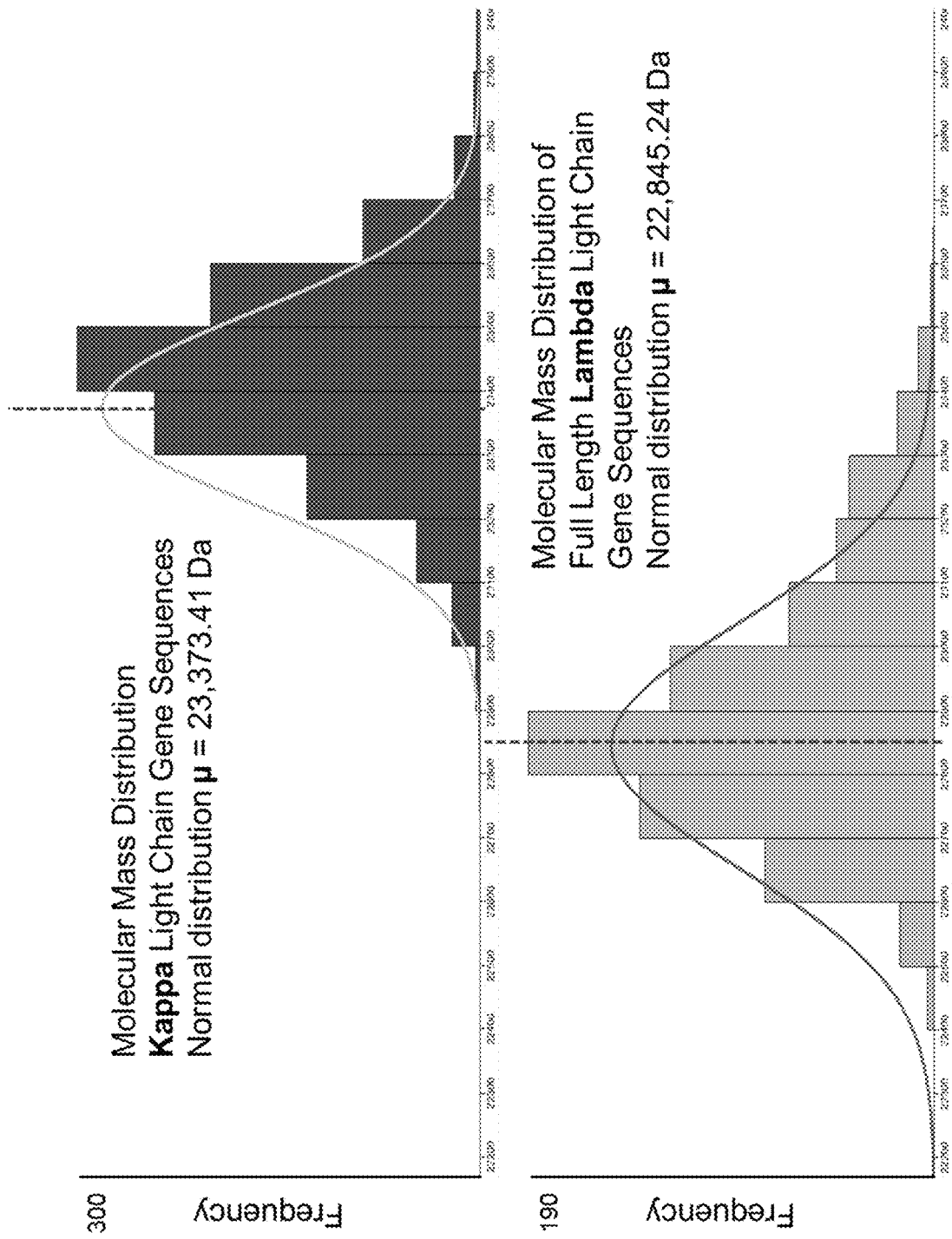
FIG. 3 shows the histograms constructed for kappa and lambda using the calculated molecular masses displayed in 100 Da bin widths.

FIG. 1 presents an example of the expected theoretical molecular mass profiles that would be observed for each of the three regions (V, J, and C) for both the kappa and lambda light chains. The profiles under the V and J regions show the predicted normal distribution of the molecular mass profiles of the translated regions while the profiles under the C regions show single bars. Since the kappa constant region has only one conserved amino acid sequence it is represented by a single molecular mass bar while the profile under the C region for lambda shows four different bars, each representing the four different lambda constant region molecular masses L1, L2, L3, and L7 (McBride, O W et al. *J Exp Med* 1982; 155:1480-90). FIG. 2 shows the amino acid sequences for the constant regions for kappa (SEQ ID NO:1) and lambda light chains (L1: SEQ ID NO:2; L2: SEQ ID NO:3; L3: SEQ ID NO:4; and L7: SEQ ID NO:5) along with the molecular mass difference between the kappa constant region and the average mass of the four lambda constant regions. Assuming that the molecular masses of the V and J region amino acid sequences follow a normal distribution, then the difference between μ for kappa and μ for lambda from their molecular mass profiles should differ by the mass difference of the constant regions (approximately 363.55 Da). Using a light chain gene sequence database containing the entire V and J regions for 1087 kappa and 735 lambda light chain sequences the molecular mass of the kappa and lambda light chains was calculated. The nucleotide sequence information for each VJ region was converted to the amino acid sequence and then converted to molecular mass. The VJ region molecular mass was then added to the molecular mass of the corresponding kappa or lambda constant region. FIG. 3 shows the histograms constructed for kappa and lambda using the calculated molecular masses displayed in 100 Da bin widths. The mean molecular mass for kappa was found to be 23,373.41 Da while the mean molecular mass for lambda was found to be 22,845.24 Da (mean indicated by vertical red dashed lines). This translates into a difference of 528.17 Da between kappa and lambda light chains which is greater than the difference of 363.55 Da between the molecular masses of the kappa and lambda constant regions alone. This difference is likely due to the contribution in mass from the framework regions (FR) within the V regions which do not undergo complete randomization compared to the complimentary determining regions (CDR) within the V regions.

As with the immunoglobulin light chains, the heavy chains include a variable and a contact region. Using known sequences selected immunoglobulin heavy chains (i.e., IgA, IgG, and IgM), the variable region gene sequences were converted to their respective amino acid sequence and then converted to a molecular mass. These masses were then added to the known constant regions molecular masses for IgA, IgG, and IgM. A set of possible molecular mass bins were made at 200 Da increments and the numbers of clones matching the mass for each bin were recorded. A smoothed histogram plot of the number of clones in each bin (y-axis) vs. molecular mass of each bin (x-axis) is shown in FIG. 2 where the red line (first and third peaks from the left)=IgA, the blue line (second and fourth peaks form the left)=IgG, and the green line (fifth and sixth peaks from the left)=IgM. The plot demonstrates that there exists a gap in the molecular mass of each of the different heavy chain isotypes analogous to the difference in mass between kappa and lambda light chains. The average known molecular mass of the constant regions for the Ig isotypes are:

IgA, 2 subclasses, Average Molecular Mass=37,090 Da
IgG, 4 subclasses, Average Molecular Mass=37,308 Da
IgM, 1 class, Molecular Mass=49,307 Da The observed molecular mass for each of the immunoglobulin isotypes will be shifted due to the addition of N-linked and/or O-linked glycosylation. This post translational modification is a natural process performed by the B cell but the extent of the glycosylation added by the cell is different for each Ig isotype and therefore should give an additional means of identifying the isotype without performing additional MS/MS fragmentation. The isotype glycosylation patters are:

IgA has both O-linked and N-linked glycosylation
IgG has only N-linked glycosylation at Aps 297
IgM has 5 N-linked glycosylation sites.

The data provided herein shows that the molecular mass distributions observed using the methods described herein represent the entire polyclonal heavy and light chain repertoire present in the serum. The ability to observe the entire immunoglobulin molecular mass distribution is a unique property of the methods provided herein and allows for the user to record a specific phenotypic immunoglobulin signature for a sample.

Figure 14:
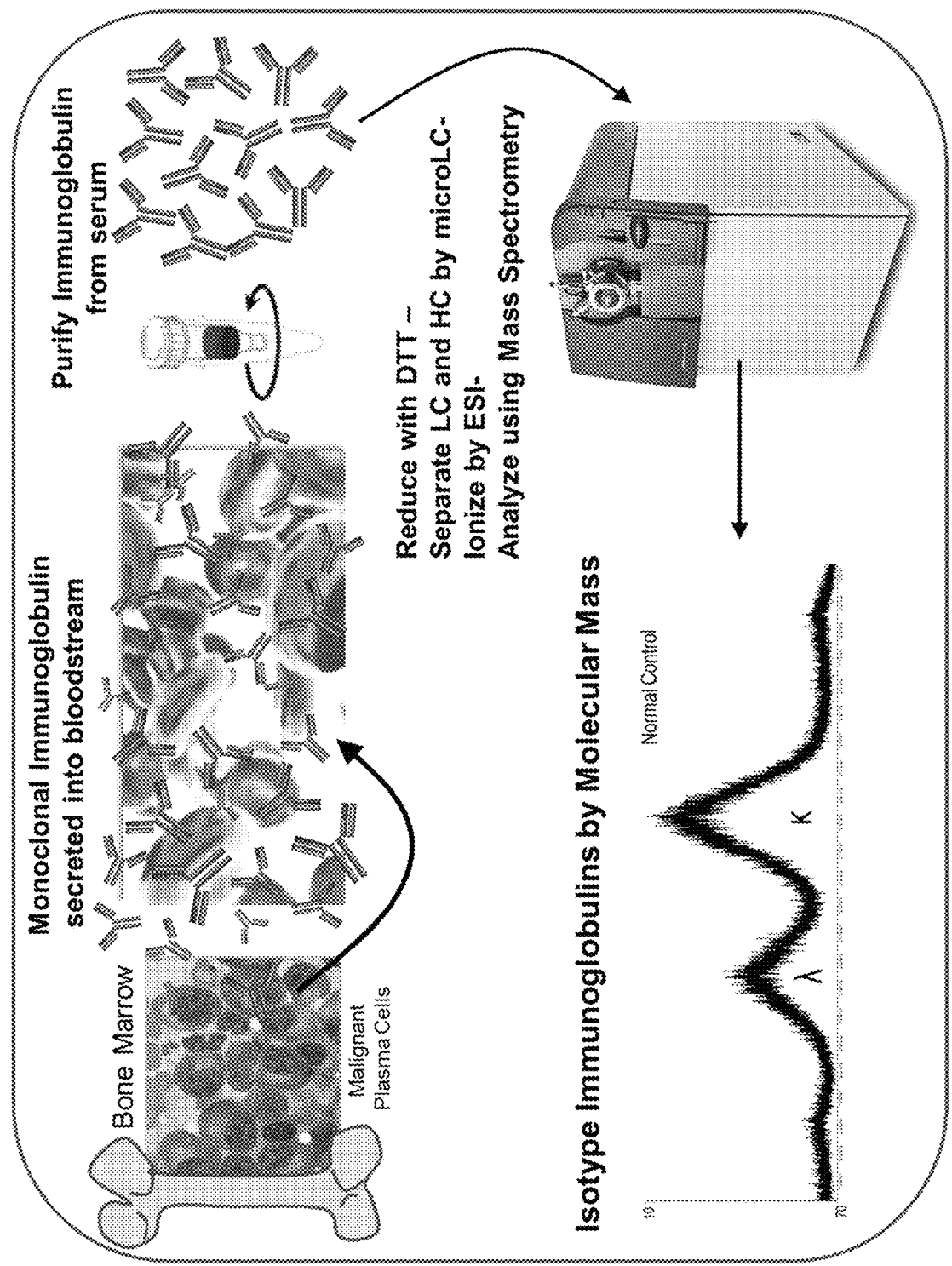
FIG. 14 is a flow chart of an embodiment of the methods provided herein.

Using the distinct molecular mass profiles of the various heavy and light chain isoptypes, a method for using mass spectrometry to identify and quantitate the heavy and light immunoglobulin chains in a sample has been discovered. For example, provided herein are methods of using this difference in molecular masses to identify and quantify the kappa and lambda light chains in samples using mass spectrometry techniques (see FIG. 14). The speed, sensitivity, resolution, and robustness of mass spectrometry makes the present methods superior than PEL, nephelometry, or IFE for isotyping immunoglobulins and allows for comparisons and quantifications of their relative abundance. Such methods are useful for diagnosing various disorders and for monitoring patients following treatment.

Protein electrophoresis can used be to quantitate CSF immunoglobulins in patients with multiple sclerosis (MS). See e.g., Kabat E A, Moore D H, Landow H. *J Clin Invest.* 1942 September; 21(5):571-7. Clinical laboratories now assess CSF with isoelectric focusing gel electrophoresis followed by IgG immunoblotting (IgG IEF) to detect IgG clones in CSF as compared to serum. See e.g., Fortini A S, Sanders E L, Weinshenker B G, Katzmann J A. *Am J Clin Pathol.* 2003 November; 120(5):672-5. Multiple CSF bands (i.e. oligoclonal bands—OCB) that are not present in serum suggest that B cell clones are actively producing IgG as part of an inflammatory response in the CNS. Detection of OCB is a sensitive method for CSF inflammatory diseases, and in multiple sclerosis, 95% of patients have IgG CSF-specific OCB. See e.g., Awad A, Hemmer B, Hartung H P, Kieseier B, Bennett J L, Stuve O. *J Neuroimmunol.* 2010 Feb. 26; 219(1-2):1-7. IgG IEF immunoblots are interpreted as; 1) No bands in serum and CSF (Negative); 2) Matching bands in serum and CSF (Negative); 3) Unique bands in serum (Negative); or 4) Unique bands in CSF (Positive). Further, isolated IgG molecules from CSF fluid have been analyzed by IEF gels, with the bands subsequently excised and then analyzed by MALD-TOF MS. See e.g., Obermeier et al. *Nature Medicine.* 2008 June; 14(6):688-93. Likewise, CSF has been purified from CSF using SDS-PAGE, with relevant bands excised, trypsinized, and measured with LC-MS. See e.g., Singh et al. Cerebrospinal-fluid-derived Immunoglobulin G of Different Multiple Sclerosis Patients Shares Mutated Sequences in Complementary Determining Regions. *Mol Cell Proteomics.* 2013 December; 12(12): 3924-34.

Using mass spectrometry methods as provided herein, also referred to as monoclonal immunoglobulin Rapid Accurate Mass Measurement (miRAMM), oligoclonal immunoglobulins can be detected by assessing their associated light chains in cerebral spinal fluid (CSF) and serum. For example, the findings for 56 paired CSF and serum samples analyzed by IgG IEF and miRAMM were compared. The two methods were in agreement with 54 samples having concordant results (22 positive and 34 negative) and 2 that were positive by IgG IEF but negative by miRAMM. Furthermore, in addition to identifying clonal immunoglobulins, the methods provided herein can be used to quantitate the amount of clonal immunoglobulin.

In various embodiments, the methods provided herein exhibit increased accuracy of clone matching between serum and CSF as compared to other known methodologies. In various embodiments, the methods have a lower supply costs as compared to immunofixation (IFE) based techniques. In various embodiments, the methods can advantageously quantitate one or more of the CSF clones.

Plasma cells (PCs) reside in the bone marrow and secrete vast quantities of high-affinity antigen specific immunoglobulins. In plasma cell dyscrasias (PCDs) there is over-representation of specific clonal PCs secreting unique M-proteins with defined masses determined by the isotype of the heavy and/or light chain composing the M-protein. These M-proteins are thus biomarkers of PCDs. Thus, if there is clinical suspicion of a PCD disorder, the patient's serum and urine is typically tested for the presence of M-proteins (also known as monoclonal immunoglobulins). M-proteins are typically detected using a combination of protein gel electrophoresis (PEL) and immunofixation.

Samples and Sample Preparation

A sample for analysis can be any biological sample, such as a tissue (e.g., adipose, liver, kidney, heart, muscle, bone, or skin tissue) or biological fluid (e.g., blood, serum, plasma, urine, lachrymal fluid, saliva, or central spinal fluid) sample. The biological sample can be from a subject that has immunoglobulins, which includes, but is not limited to, a mammal, e.g. a human, dog, cat, primate, rodent, pig, sheep, cow, and horse. In some embodiments, the biological sample comprises an exogenous monoclonal immunoglobulin. A sample can also be a man-made reagent, such as a mixture of known composition or a control sample.

A sample can be treated to remove components that could interfere with the mass spectrometry technique. A variety of techniques known to those having skill in the art can be used based on the sample type. Solid and/or tissue samples can be ground and extracted to free the analytes of interest from interfering components. In such cases, a sample can be centrifuged, filtered, and/or subjected to chromatographic techniques to remove interfering components (e.g., cells or tissue fragments). In yet other cases, reagents known to precipitate or bind the interfering components can be added. For example, whole blood samples can be treated using conventional clotting techniques to remove red and white blood cells and platelets. A sample can be deproteinized. For example, a plasma sample can have serum proteins precipitated using conventional reagents such as acetonitrile, KOH, NaOH, or others known to those having ordinary skill in the art, optionally followed by centrifugation of the sample.

Immunoglobulins can be isolated from the samples or enriched (i.e. concentrated) in a sample using standard methods known in the art. Such methods include removing one or more non-immunoglobulin contaminants from a sample. In some embodiments, the samples can be enriched or purified using immunopurification, centrifugation, filtration, ultrafiltration, dialysis, ion exchange chromatography, size exclusion chromatography, protein A/G affinity chromatography, affinity purification, precipitation, gel electrophoresis, capillary electrophoresis, chemical fractionation (e.g., antibody purification kits, such as Melon Gel Purification), and aptamer techniques. For example, the immunoglobulins can be purified by chemical-based fractionation, e.g., Melon Gel Chromatography (Thermo Scientific), where Melon Gel resins bind to non-immunoglobulin proteins in a sample and allow immunoglobulins to be collected in the flow-through fraction; or by affinity purification, e.g., by Protein A, Protein G, or Protein L purification, where immunoglobulins are bound by those proteins at physiologic pH and then released from the proteins by lowering the pH. When serum, plasma, or whole blood samples are used, a sample, such as a 10-250 µl sample, e.g., a 50 µl, can be directly subjected to Melon Gel, Protein A, Protein G, or Protein L purification. Size exclusion principles such as a TurboFlow column can also be employed to separate the non-immunoglobulin contaminants from a sample. When urine samples are used, a urine sample can be buffered, e.g., a 50 µl urine sample can be diluted first with 50 µl of 50 mM ammonium bicarbonate.

In some embodiments, a sample can be subject to immunopurification prior to analysis by mass spectrometry. In some embodiments, the sample can be immunoglobulin enriched. For example, immunopurification can result in enrichment of one or more immunoglobulins. In some embodiments, immunopurification can separate or enrich immunoglobulin light chains in a sample. In some embodiments, immunopurification can separate or enrich immunoglobulin heavy chains in a sample. In some embodiments, immunopurification can separate or enrich immunoglobulin kappa light chains or immunoglobulin lambda light chains in a sample. In some embodiments, immunopurification can separate or enrich IgG, IgA, IgM, IgD, or IgE in a sample. Immunopurification can involve contacting a sample containing the desired antigen with an affinity matrix including an antibody (e.g. single domain antibody fragments) to the antigen covalently attached to a solid phase (e.g., agarose beads). Antigens in the sample become bound to the affinity matrix through an immunochemical bond. The affinity matrix is then washed to remove any unbound species. The antigen is then removed from the affinity matrix by altering the chemical composition of a solution in contact with the affinity matrix. The immunopurification may be conducted on a column containing the affinity matrix, in which case the solution is an eluent or in a batch process, in which case the affinity matrix is maintained as a suspension in the solution.

In some embodiments, single domain antibody fragments (SDAFs) with an affinity for immunoglobulins can be used in the immunopurification process. SDAFs can be derived from heavy chain antibodies of non-human sources (e.g., camelids), heavy chain antibodies of human sources, and light chain antibodies of humans. SDAFs possess unique characteristics, such as low molecular weight, high physical-chemical stability, good water solubility, and the ability to bind antigens inaccessible to conventional antibodies.

Employing the combination of enrichment using a collection of antibodies (e.g., single domain antibody fragments) with affinity for one or more of the different immunoglobulin isotypes coupled with rapid generation of mass spectra using MALDI-TOF mass spectrometry, it was discovered that identification of monoclonal proteins, quantitation of M-proteins, and identification of one or more of the heavy or light chain immunoglobulins, including identification of the heavy/light chain isotype pairings. The methods provided herein can generate clinical information equivalent to the four currently used clinical assays for diagnosis and monitoring PCDs-PEL, total protein quantitation, IFE and Hevy Lite (HCL) assays could be accomplished.

In some embodiments, isolation of immunoglobulins can be performed with an entity other than a traditional antibody—which contains both heavy and light chains (such as those used in IFE and various known clinical immunoassays). Traditional antibodies contain heavy and/or light chains with masses that may overlap with the masses of the immunoglobulins in the sample of interest (e.g., human immunoglobulins). Therefore, these antibodies may interfere in the mass spectra of the patient's immunoglobulins. Single domain antibody fragments (SDAFs) may have masses ranging from 12,500-15,000 Da and, using the methods described herein, may carry a single charge thus generating a signal in the range of 12,500-15,000 m/z, which does not overlap with the signals generated by human heavy chains or light chains. Also, accurate molecular mass alone is not 100% specific in identification of immunoglobulin isotype as there are m/z regions (23,000-23,200 m/z or 11,500-11,600 m/z) where immunoglobulins may be of the kappa or lambda light chain isotype. Thus, in some embodiments, the use of specific isolation of heavy and/or light chains utilizing SDAFs, coupled with mass identification, results in a specific and sensitive method for the detection of immunoglobulin heavy chains and immunoglobulin light chains.

In various embodiments, the use of single domain antibody fragments may be used in place of concentrating samples with low concentrations of immunoglobulins prior to analysis. In various some embodiments, the method described herein can replace the need for total protein measurement and protein gel electrophoresis of urine or serum in order to quantitate specific monoclonal proteins. In various embodiments, the method can identify all the major types of monoclonal isotypes of M-proteins with sensitivity exceeding current methods. In various embodiments, the method is faster, less expensive, less laborious, and automatable. In various embodiments, the method is advantageous because it creates an electronic record as opposed to a gel. In various embodiments, the method overcomes the shortcoming of previous methods in that data acquisition can take less than 15 seconds per sample.

In some embodiments, the immunoglobulins, or the heavy and/or light chains thereof, are substantially isolated. By "substantially isolated" is meant that the immunoglobulins are at least partially or substantially separated from the sample from which they were provided. Partial separation can include, for example, a sample enriched in the immunoglobulins (i.e., the heavy and/or light chains). Substantial separation can include samples containing at least about 10%, at least about 20%, at least about 30%, at least about 40%, at least about 50%, at least about 60%, at least about 70%, at least about 80%, at least about 90%, at least about 95%, at least about 97%, or at least about 99% by weight of the immunoglobulin, or the heavy and/or light chains thereof. Methods for isolating immunoglobulins, such as those described above, are routine in the art.

Intact immunoglobulins can be further processed to decouple the light chains in a total immunoglobulin sample from the heavy chain immunoglobulins. Decoupling can be achieved by treating the total immunoglobulins with a reducing agent, such as DTT (2,3 dihydroxybutane-1,4-dithiol), DTE (2,3 dihydroxybutane-1,4-dithiol), thioglycolate, cysteine, sulfites, bisulfites, sulfides, bisulfides, TCEP (tris(2-carboxyethyl)phosphine), 2-mercaptoethanol, and salt forms thereof. In some embodiments, the reducing step is performed at elevated temperature, e.g., in a range from about 30° C. to about 65° C., such as about 55° C., in order to denature the proteins. In some embodiments, the sample is further treated, e.g., by modifying the pH of the sample or buffering the sample. In some embodiments, the sample can be acidified. In some embodiments, the sample can be neutralized (e.g., by the addition of a base such as bicarbonate).

Mass Spectrometry Methods

After sample preparation, an immunoglobulin sample, such as a decoupled sample having one or more heavy or light immunoglobulin chains, can be subjected to a mass spectrometry (MS) technique, either directly or after separation on a high performance liquid chromatography column (HPLC). In some embodiments, liquid chromatography mass spectrometry (LC-MS) can be used to analyze the mass spectrum of the ions. For example, the method can be used to identify multiply charged ions (e.g., the +1 ions, +2 ions, +3 ions, +4 ions, +5 ions, +6 ions, +7 ions, +8 ions, +9 ions, +10 ions, +11 ions, +12 ions, +13 ions, +14 ions, +15 ions, +16 ions, +17 ions, +18 ions, +19 ions, +20 ions, +21 ions, and +22 ions), resulting from the heavy or light chains in the sample. In some embodiments, the +11 charged ion is identified and used for further analysis. In some embodiments, the samples are not fragmented during the mass spectrometry technique. LC-MS is an analytical technique that combines the physical separation capabilities of liquid chromatography with the mass analysis capabilities of mass spectrometry, and is suitable for detection and potential identification of chemicals in a complex mixture. Any LC-MS instrument can be used, e.g., the ABSciex 5600 Mass Spectrometer. In some embodiments, microflowLC-MS can be utilized. Any suitable microflow instrument can be used, e.g., the Eksigent Ekspert 200 microLC. The ion mass spectrum can be analyzed for one or more peaks corresponding to one or more heavy or light chains in the sample. For example, one or more ion peaks, e.g., a +11 ion peak for each of the kappa and lambda light chains, can be examined to determine the ratio of each chain in the sample. In some embodiments, the ratio is determined by the peak area of the selected ion peak(s).

In some embodiments, electrospray ionization coupled to a quadrupole time-of-flight mass spectrometry (ESI-Q-TOF MS) can be used to analyze the mass spectrum of an immunoglobulin sample, e.g., the mass spectrum of the +11 charge state of the heavy and/or light chains in the sample. Electrospray ionization mass spectrometry (ESI MS) is a useful technique for producing ions from macromolecules because it overcomes the propensity of these molecules to fragment when ionized. In addition, ESI often produces multiply charged ions, effectively extending the mass range of the analyzer to accommodate the orders of magnitude observed in proteins and other biological molecules. A quadrupole mass analyzer (Q) consists of four cylindrical rods, set parallel to each other. In a quadrupole mass spectrometer, the quadrupole is the component of the instrument responsible for filtering sample ions based on their mass-to-charge ratio (m/z). The time-of-flight (TOF) analyzer uses an electric field to accelerate the ions through the same potential, and then measures the time they take to reach the detector. If the particles all have the same charge, the kinetic energies are identical, and their velocities depend only on their masses. Lighter ions reach the detector first.

Any ESI-Q-TOF mass spectrometer can be used, e.g., the ABSciex TripleTOF 5600 quadrupole time-of-flight mass spectrometer. The mass spectrum, e.g., the mass spectrum of multiply charged intact light chain or heavy chain polypeptide ions, can be analyzed to identify one or more peaks at an appropriate mass/charge expected for the chain. For example, for the light chains, the peaks can occur at about 600-2500 m/z. In some embodiments, the peaks can occur at about 1000-2300 m/z (e.g., about 2000-2200 m/z for the +11 ion). Fragment ion peaks can be detected at a range of m/z of 250-2000. In the case of the heavy chains, the peaks can occur at about 600-2500 m/z. In some embodiments, the peaks can occur at about 900-2000 m/z.

In some embodiments, electrospray ionization coupled to a quadrupole, time-of-flight orbitrap mass analyzer can be used to analyze the mass spectrum of an immunoglobulin sample, e.g., the mass spectrum of the +11 charge state of the heavy and/or light chains in the sample The multiply charged ion peaks can be converted to a molecular mass using known techniques. For example, multiply charged ion peak centroids can be used to calculate average molecular mass and the peak area value used for quantification is supplied by a software package. Specifically, multiple ion deconvolution can be performed using the Bayesian Protein Reconstruct software package in the BioAnalyst companion software package in ABSCIEX Analyst TF 1.6. The following settings can be used: Start mass (Da)=22,000, Stop mass (Da)=26,000 Da, Step mass (Da)=1, S/N threshold=20, Minimum intensity %=0, Iterations=20, Adduct: Hydrogen. A limited mass range was used with a Start m/z=1,100 and a Stop m/z=2,500. Deconvoluted and multiply charged ions can also be manually integrated using the Manual Integration 33 script in Analyst TF. Providing the molecular mass for the heavy and/or light immunoglobulin chains in the sample facilitates quantification and isotyping of the chains in the sample. For example, the methods provided herein can be used to determine the ratio of the kappa and lambda light chains in the sample. The kappa/lambda ratio is simply the calculated peak area for the kappa light chain molecular mass distribution divided by the lambda light chain molecular mass distribution. In addition, the methods provided herein can be used to compare the relative abundance of each of the light chains as compared to a control or reference sample. As will be discussed in more detail below, the accepted ratio of kappa to lambda light chains in a normal serum sample is 3.20. Deviations from this ratio can be indicative of various disorders and therefore is a useful tool for diagnosing and monitoring patients with such disorders.

In some embodiments, matrix assisted laser adsorption ionization-time of flight mass spectrometry (MALDI-TOF MS) can be used to analyze the mass spectrum of an immunoglobulin sample. MALDI-TOF MS identifies proteins and peptides as mass charge (m/z) spectral peaks. Further, the inherent resolution of MALDI-TOF MS allows assays to be devised using multiple affinity ligands to selectively purify/concentrate and then analyze multiple proteins in a single assay.

Methods for Screening Biological Samples and for Diagnosing and Monitoring Disorders The mass spectrometry based methods provided herein can be used to determine the ratio of the kappa and lambda immunoglobulin light chains in a sample. In some embodiments, a sample (e.g., a biological sample) having one or more immunoglobulins can be subjected to a mass spectrometry assay. The sample can be pretreated to isolate or enrich immunoglobulins present in the sample and in some cases; the immunoglobulin light chains can be decoupled from the immunoglobulin heavy chains prior to the mass spectrometry analysis. The spectrum obtained from the assay can then be used to determine the ratio of the kappa and lambda immunoglobulin light chains in the sample. In some embodiments, the relative abundance of the kappa and lambda light chains can be determined by converting the peak areas of one or more of the identified peaks into a molecular mass.

The ratios and relative abundance of the immunoglobulin light chains can be compared to a reference value or a control sample to aid in the diagnosis of various disorders, including polyclonal gammopathies (e.g., hypergammaglobulinemia), autoimmune disorders (e.g., Sjögren's syndrome), infectious disorders (e.g., HIV) and inflammatory disorders (e.g., chronic inflammatory disorders). In such disorders, the ratio of kappa to lambda immunoglobulin light chains is skewed from the accepted normal ratio (e.g., a ratio of 3.20). For example, in the case of an autoimmune disorder such as Sjögren's syndrome, the prevalence of kappa immunoglobulin light chains is increased from normal and the ratio of kappa to lambda light chains is higher than the normal 3.20, for example, the ratio can be about 5 (e.g., 83:17). For an inflammatory disorder such as a chronic inflammatory disorder, the relative abundance of each of the light chains can be reversed (i.e. a higher prevalence of the lambda light chain as compared to the kappa light chain is observed). For example, the amount of lambda light chains in a sample from a patient suffering from such a disorder can be about 0.5 (e.g., 0.54). In some cases, disorders such as hypergammaglobulinemia can be diagnosed based on the relative abundance of the immunoglobulin light chains as compared to a reference value or control sample. For example, the relative abundance of the light chains compared to a reference value accepted as normal can be at least two standard deviations higher; in some cases, at least 50% greater, at least 75% greater, or at least 100% greater, or at least 2-fold higher, 3-fold higher, or 4-fold, or more. In addition to relative ratios, the detection of immunoglobulin clones which appear in greater quantities than the polyclonal background can aid in the diagnosis of disease state. For example, patients who are responding to a bacterial infection are known to produce oligoclonal immunoglobulin response towards that bacterial. Observation of an oligoclonal response can then direct the treatment toward infectious agents.

In some embodiments, the methods provided herein can be used to confirm a diagnosis made by current methods such as protein electrophoresis (PEL) or immunofixation (IF) test. For example, if a negative result is obtained from PEL and/or IF, the present methods can be used as a secondary test to confirm or counter such results. In some embodiments, the diagnosis provided herein can be confirmed using such standard methods.

The mass spectrometry based methods provided herein can also be used for monitoring the treatment of a disorder in a subject. For example, when the subject is diagnosed to have polyclonal gammopathy (e.g., hyperglobulinemia), the methods provided herein can further be used to monitor a treatment of polyclonal gammopathy. Such methods include providing a first sample of the subject before the treatment and a second sample of the subject during or after the treatment. Immunoglobulins can be isolated or enriched from the first and second samples, and subjected to a mass spectrometry technique. The ratio of the kappa and lambda light chains is determined before and after the treatment and compared. A shift of the ratio toward the accepted normal value indicates that the treatment may be effective for the subject; while an increased change or no change in the ratio indicates that the treatment may be ineffective for the subject.

The techniques provided herein can also be used to differentiate human samples from those of other mammalian species based on the relative distribution of the kappa and lambda light chains. Such methods may be useful for prescreening biological samples used in, for example, anti-doping testing.

In addition, the methods provided herein are useful for identifying the isotype of the heavy and or light chain immunoglobulins. In certain diseases, such as multiple myeloma, there is an increase in the amount of a monoclonal immunoglobulin in the bloodstream. If high levels of the monoclonal immunoglobulin are detected, additional tests are performed to determine the isotypes of the heavy and light chains of the monoclonal immunoglobulin. Current methods use anti-constant region antibodies to determine the isotype. The methods provided herein provide an alternative to current methods and show superior speed, sensitivity, resolution, and robustness than the conventional laboratory tests.

In some embodiments, the methods provided herein can be used to diagnose inflammatory diseases of the central nervous system (CNS). Examples of CNS inflammatory diseases that may be diagnosed using methods provided herein include multiple sclerosis, neuromyelitus optica, neurosarcoidosis, subacute sclerosing panencephalitis, and Guillian-Barrre Syndrome. The methods provided herein can be used to detect immunoglobulins located with the cerebral spinal fluid (CSF) of a subject (e.g., a patient). In some embodiments, the method includes (a) providing a cerebral spinal fluid (CSF) sample comprising one or more immunoglobulins; (b) subjecting the CSF sample to a mass spectrometry technique to obtain a mass spectrum of the CSF sample; and (c) identifying a mass peak corresponding to one or more light chains in the CSF sample.

Prior to subjecting the CSF sample to a mass spectrometry technique to obtain a mass spectrum of the CSF sample, the CSF sample can be diluted with a solution (e.g., buffer). For example, the CSF sample can be diluted to about 1:5, 1:3, 1:1, 3:1, or about 5:1 with buffer or other solution. In some embodiments, the CSF sample is diluted to about 1:1 with buffer or other solution. Further, prior to subjecting the serum sample to a mass spectrometry technique the immunoglobulins in the serum can be enriched with a Melon gel as described previously.

EXAMPLES

General Methods.
Serum and Immunoglobulin Reagents:
Serum was collected from waste samples obtained from the clinical laboratory. Purified IgG kappa and IgG lambda from normal donors was purchased from Bethyl Laboratories (Montgomery, Tex.).
Reagents:
Ammonium bicarbonate, dithiothreitol (DTT), and formic acid were purchased from Sigma-Aldrich (St. Louis, Mo.). Melon Gel was purchased from Thermo-Fisher Scientific (Waltham Mass.). Water, acetonitrile, and 2-propanol were purchased from Honeywell Burdick and Jackson (Muskegon, Mich.).
Serum:
A volume of 50 µL of serum was enriched for immunoglobulins using Melon Gel following the manufacturer's instructions. After immunoglobulin enrichment, 25 µL of sample was reduced by adding 25 µL of 100 mM DTT and 25 µL of 50 mM ammonium bicarbonate then incubated at 55° C. for 15 minutes before injection. Samples were placed into 96 deep-well PCR plates (300 µL volume) at 9° C. while waiting for injection.
LC Conditions:
An Eksigent Ekspert 200 microLC (Dublin, Calif.) was used for separation; mobile phase A was water+0.1% formic acid (FA), and mobile phase B was 90% acetonitrile+10% 2-propanol+0.1% FA. A 2 µL injection was made onto a 1.0×75 mm Poroshell 300SB-C3, 5 µm particle size column flowing at 25 µL/minute while the column was heated at 60° C. A 25 minute gradient was started at 80% A/20% B, held for 1 minute, ramped to 75% A/25% B over 1 minutes, then ramped to 65% A/35% B over 10 minutes, then ramped to 50% A/50% B over 4 minutes, then ramped to 95% A/5% B over 2 minutes held for 5 minutes, then ramped to 80% A/20% B over 1 minute, then equilibrating at 80% A/20% B for 1 minute.
ESI-Q-TOF MS:
Spectra were collected on an ABSciex TripleTOF 5600 quadrupole time-of-flight mass spectrometer (ABSciex, Vaughan ON, CA) in ESI positive mode with a Turbo V dual ion source with an automated calibrant delivery system (CDS). Source conditions were: IS: 5500, Temp: 500, CUR: 45, GS1: 35, GS2: 30, CE: 50±5. TOF MS scans were acquired from m/z 600-2500 with an acquisition time of 100 ms. Fragment ion scans were acquired from m/z 350-2000 with an acquisition time of 100 ms. The instrument was calibrated every 5 injections through the CDS using calibration solution supplied by the manufacturer.
MS Data Analysis:
Analyst TF v1.6 was used for instrument control. Data were viewed using Analyst TF v1.6 and PeakView v1.2.0.3. Multiply charged ion peak centroids were used to calculate average molecular mass and the peak area value used for quantification through BioAnalyst software provided with Analyst TF. Multiple ion deconvolution was performed using the following BioAnalyst specific parameters: mass range of 20,000 Da and 28,000 Da, hydrogen adduct, step size of 1, S/N of 20, and 20 iterations for light chain molecular mass calculations.
Bioinformatics Data Analysis:
The normal distribution used to model the kappa and lambda light chain molecular mass profile was generated using kappa and lambda gene sequences from the Boston University ALBase. Gene sequences were uploaded into the IMGT alignment tool V-QUEST (Brochet, X et al. *Nucleic Acids Res* 2008; 36:W503-8) and each sequence was aligned from the variable (V) region Frame 1 (N-terminus) through the joining (J) region to the beginning of the constant (C) region. Only gene sequences that included the entire V region through the J region were used (46 kappa and 46 lambda). The gene sequence was then translated into the corresponding amino acid sequence using the ExPASy Translate tool. This amino acid sequence was then converted to average molecular mass using the ExPASy Compute pI/Mw tool and then added to the molecular mass of the corresponding isotype constant region. Each molecular mass was placed into 100 Da width bins and the software package JMP 10.0.0 was used to produce histograms and to calculate the mean molecular mass and to model the normal distribution of calculated molecular masses.

Figure 4:
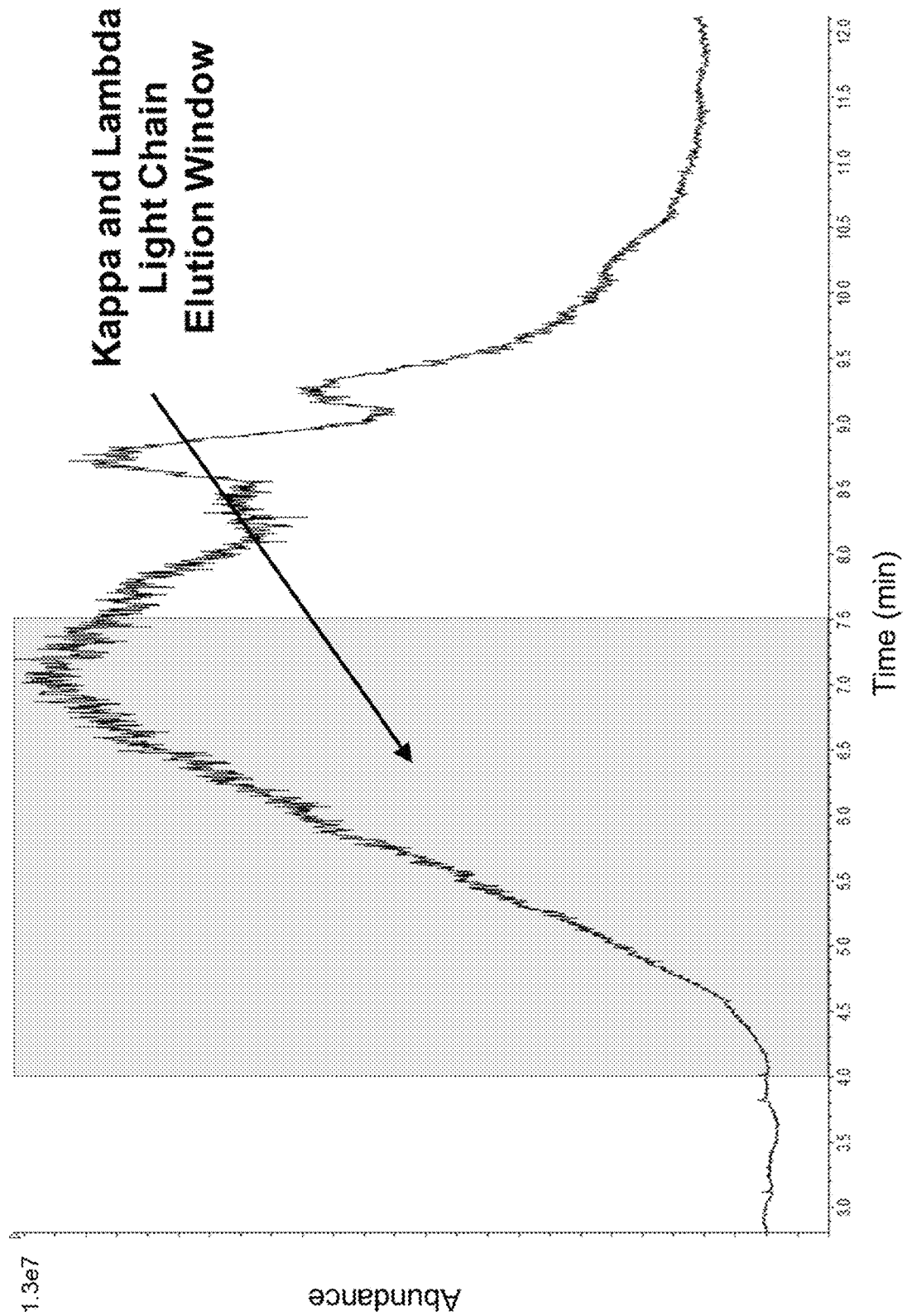
FIG. 4 shows a total ion chromatogram obtained from the injection of 2 µL melon gel purified and DTT reduced normal pooled serum analyzed by microLC-ESI-Q-TOF MS.
Figure 5:
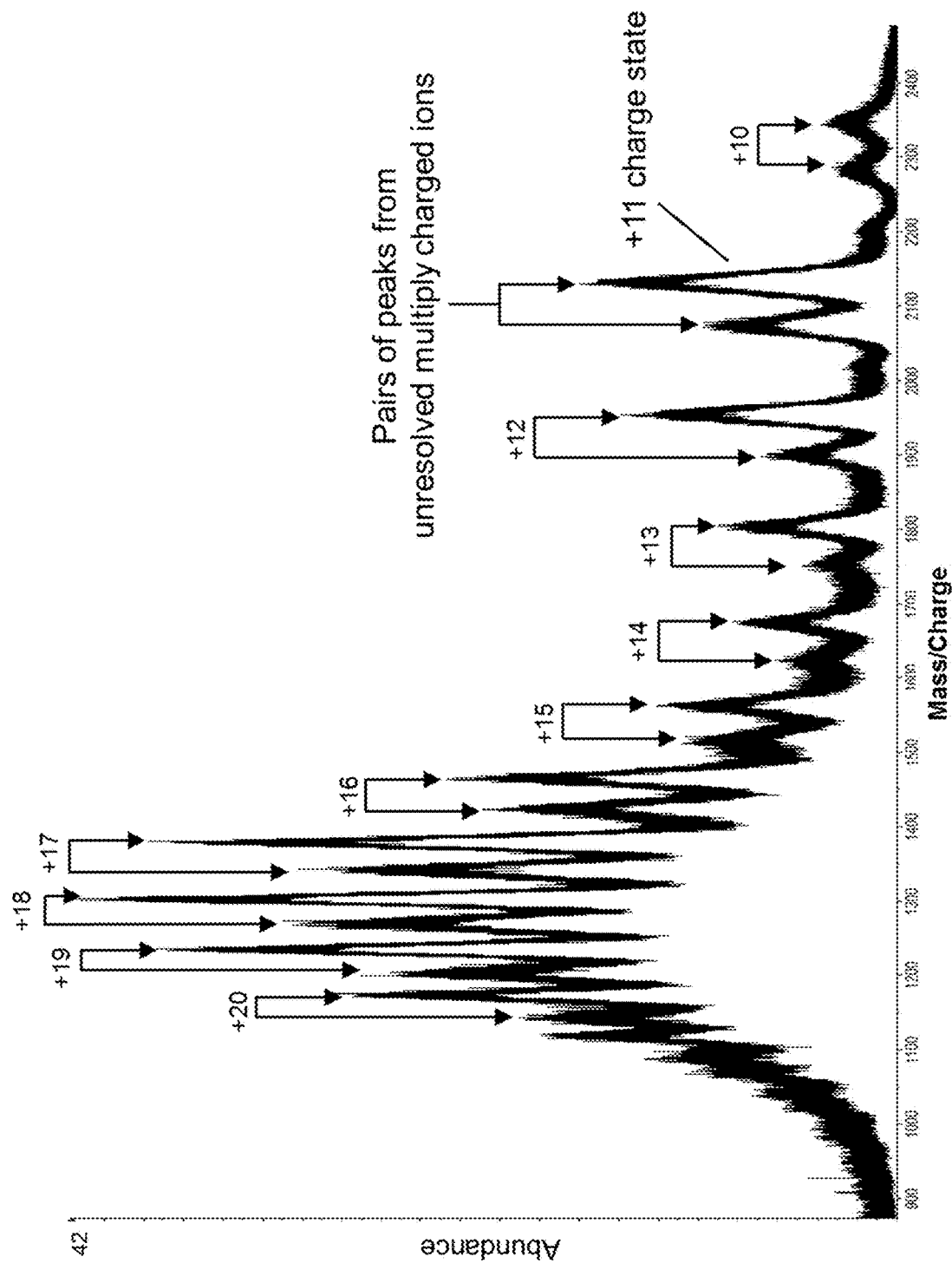
FIG. 5 shows the mass spectrum obtained by summing the spectra collected a 1 minute window with the charge state of the expected polyclonal kappa light chains shown next to the highlighted vertical line.
Figure 6:
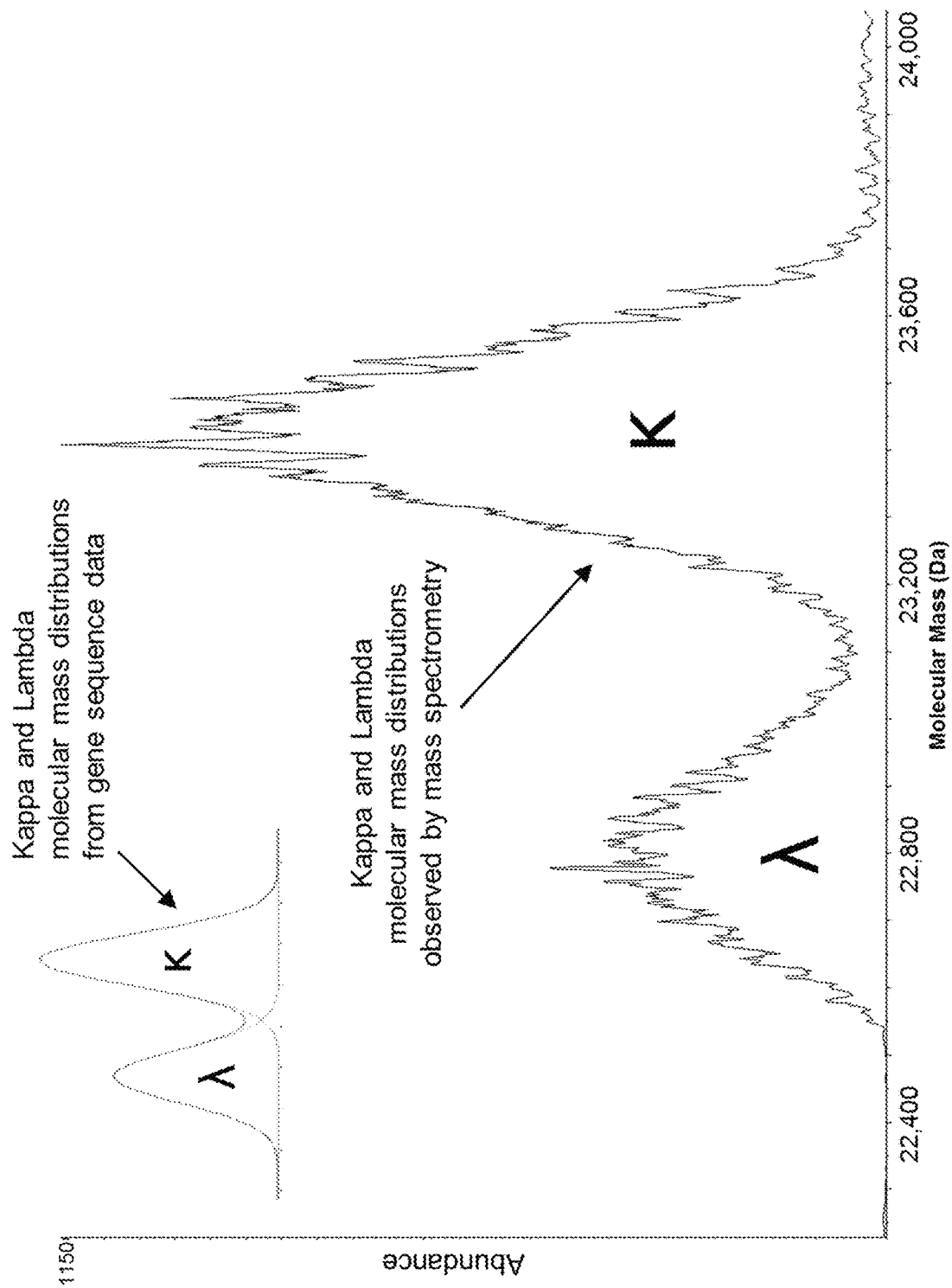
FIG. 6 provides the deconvoluted mass spectrum of FIG. 5 transformed to molecular mass and showing the kappa and lambda polyclonal molecular mass profile.

Example 1—Monitoring Kappa and Lambda Light Chain Repertoires in Serum Using Mass Spectrometry The inventors have discovered distinct polyclonal kappa and lambda light chain molecular mass profiles that can be used to identify and quantify kappa and lambda light chains in biological samples. FIG. 4 shows a total ion chromatogram obtained from the injection of 2 µL melon gel purified and DTT reduced normal pooled serum analyzed by microLC-ESI-Q-TOF MS and using the methods described above. The highlighted area represents the 5.0 to 6.0 minute retention time window where light chains begin to elute from the LC column. FIG. 5 shows the mass spectrum obtained by summing the spectra collected over this 1 minute window with the charge state of the expected polyclonal kappa light chains shown next to the highlighted vertical line. FIG. 5 also shows a close up view of the +11 charge state for the expected polyclonal kappa and lambda light chains. FIG. 6 shows the deconvoluted mass spectrum of FIG. 5 transformed to molecular mass and showing the kappa and lambda polyclonal molecular mass profile. The inset to FIG. 6 shows the normally distributed molecular mass profile calculated from the gene sequence data showing an excellent match to the experimentally observed molecular mass profile. The mean molecular mass calculated for the kappa polyclonal light chains was 23,433 Da while the mean molecular mass for the lambda light chains was 22,819 Da. This translates into a difference of 614 Da, 19 Da (3%) lower than the calculated difference between kappa and lambda light chains using the gene sequence data.

Example 2—Confirming Light Chain Isotype Labeling

Figure 7:
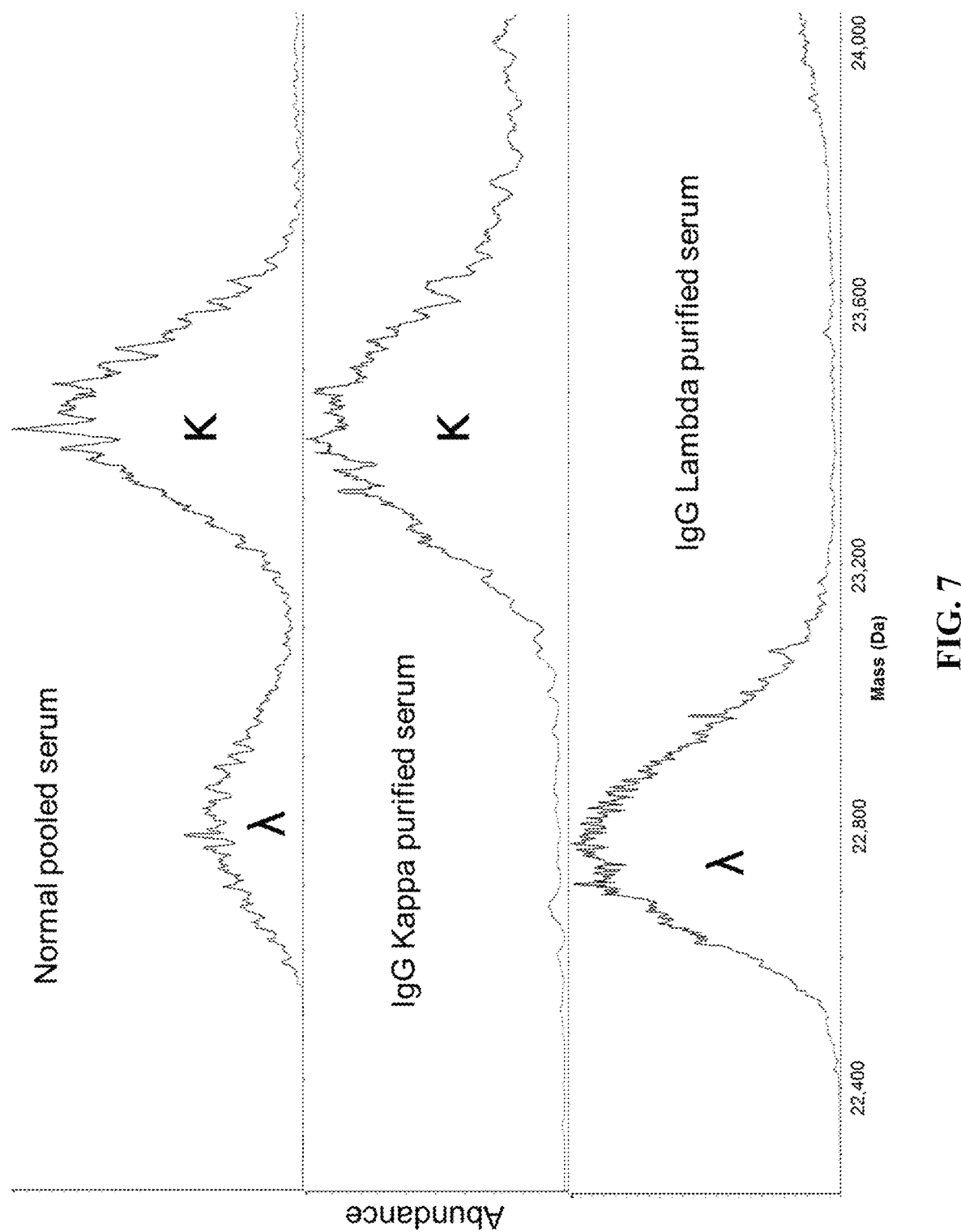
FIG. 7 shows the results comparing the deconvoluted molecular mass profiles for normal pooled serum (top), IgG kappa purified normal pooled serum (middle), and IgG lambda purified normal pooled serum (bottom).

To confirm that the two molecular mass profiles were indeed representative of the kappa and lambda light chain isotypes, commercially available purified IgG kappa and purified IgG lambda preparations obtained from pooled normal serum were analyzed by microLC-ESI-Q-TOF MS and using the methods described above. FIG. 7 shows the results comparing the deconvoluted molecular mass profiles for normal pooled serum (top), IgG kappa purified normal pooled serum (middle), and IgG lambda purified normal pooled serum (bottom). The figure clearly shows the absence of the lambda polyclonal molecular mass profile in the IgG kappa purified normal pooled serum and the absence of the kappa polyclonal molecular mass profile in the IgG lambda purified normal pooled serum. Furthermore, the IgG kappa purified and IgG lambda purified serum sample isotypes were confirmed using top-down MS as described previously (Barnidge. D R et al. *J Proteome Res* 2014). These observations support the findings that polyclonal kappa light chains in serum have a molecular mass profile between approximately 23,200 Da and 23,800 Da and polyclonal lambda light chains in serum have a molecular mass profile between approximately 22,500 Da and 23,200 Da.

In addition to providing the kappa and lambda light chain molecular mass profile, the microLC-ESI-Q-TOF MS methods provided herein also offer the relative abundance of each isotype from serum enriched for immunoglobulins and reduced with DTT. In FIG. 6, the calculated peak area for the kappa light chains was found to be $2.40 \times 10^5$ while the peak area for the lambda light chains was found to be $7.51 \times 10^4$ resulting in a kappa/lambda ratio of 3.20 similar to published findings (Haraldsson, A et al. *Ann Clin Biochem* 1991; 28 (Pt 5):461-6).

Example 3—Kappa and Lambda Measurements in Non-Human Mammalian Samples

Figure 8:
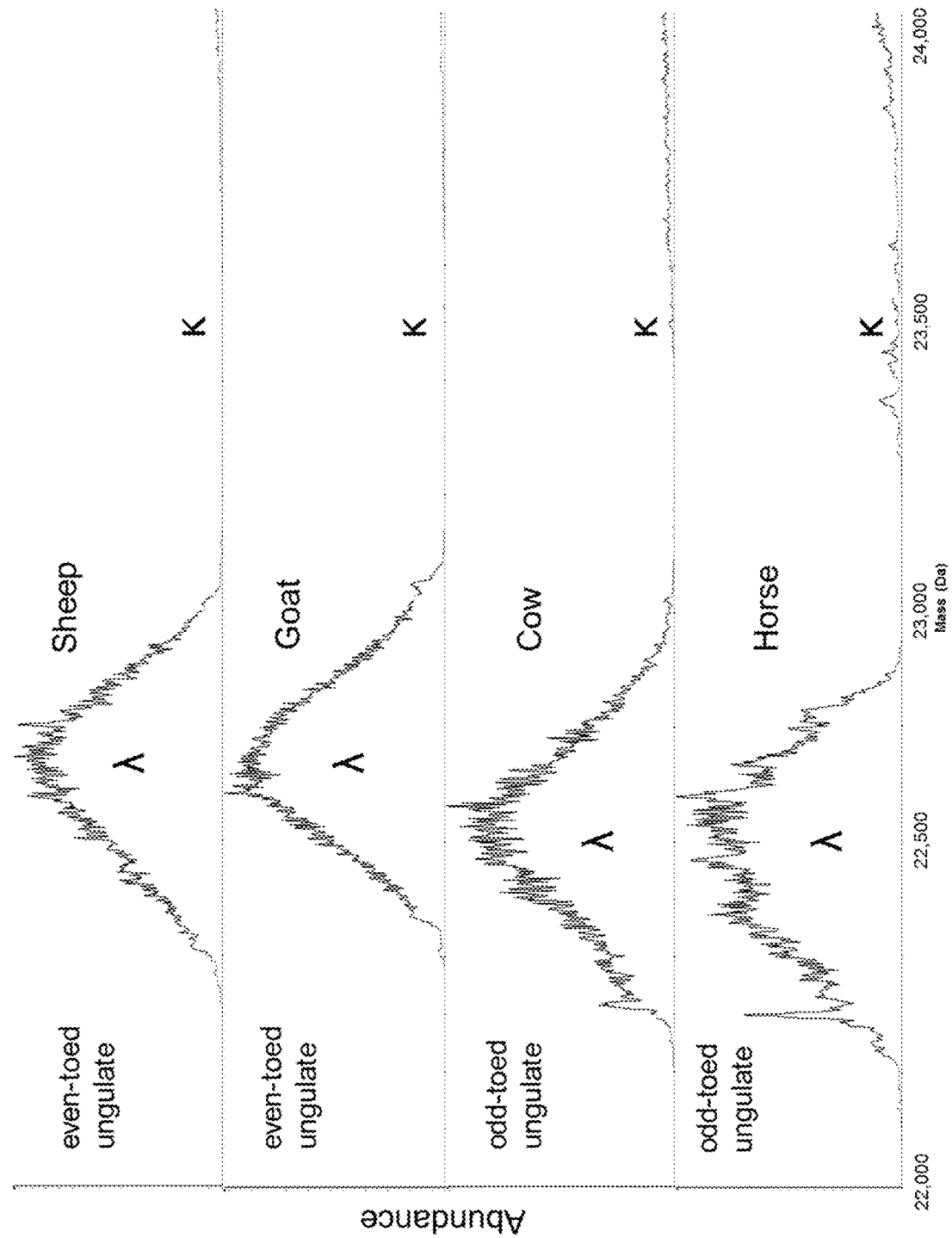
FIG. 8 provides the results for pooled serum samples derived from sheep, goats, cows, and horses.

Additional experiments were performed on serum from four other mammals to evaluate the differences in kappa/lambda expression ratios. FIG. 8 shows the results for pooled serum samples derived from sheep, goats, cows, and horses. These molecular mass profiles illustrate that sheep, goat, cow, and horse have polyclonal immunoglobulin light chain molecular mass profiles that fall into the lambda mass range. Top-down MS was performed on the sheep serum sample to confirm that the observed molecular mass profile was indeed a lambda isotype (data not shown). The observation that lambda light chains are the predominant isotype in odd and even toed ungulates is in agreement with previously published observations (Arun, S S et al. *Zentralbl Veterinarmed A* 1996; 43:573-6; Sun Y, et al. *J Anim Sci Biotechnol* 2012; 3:18; and Butler, J E et al *Dev Comp Immunol* 2009; 33:321-33).

Figure 9:
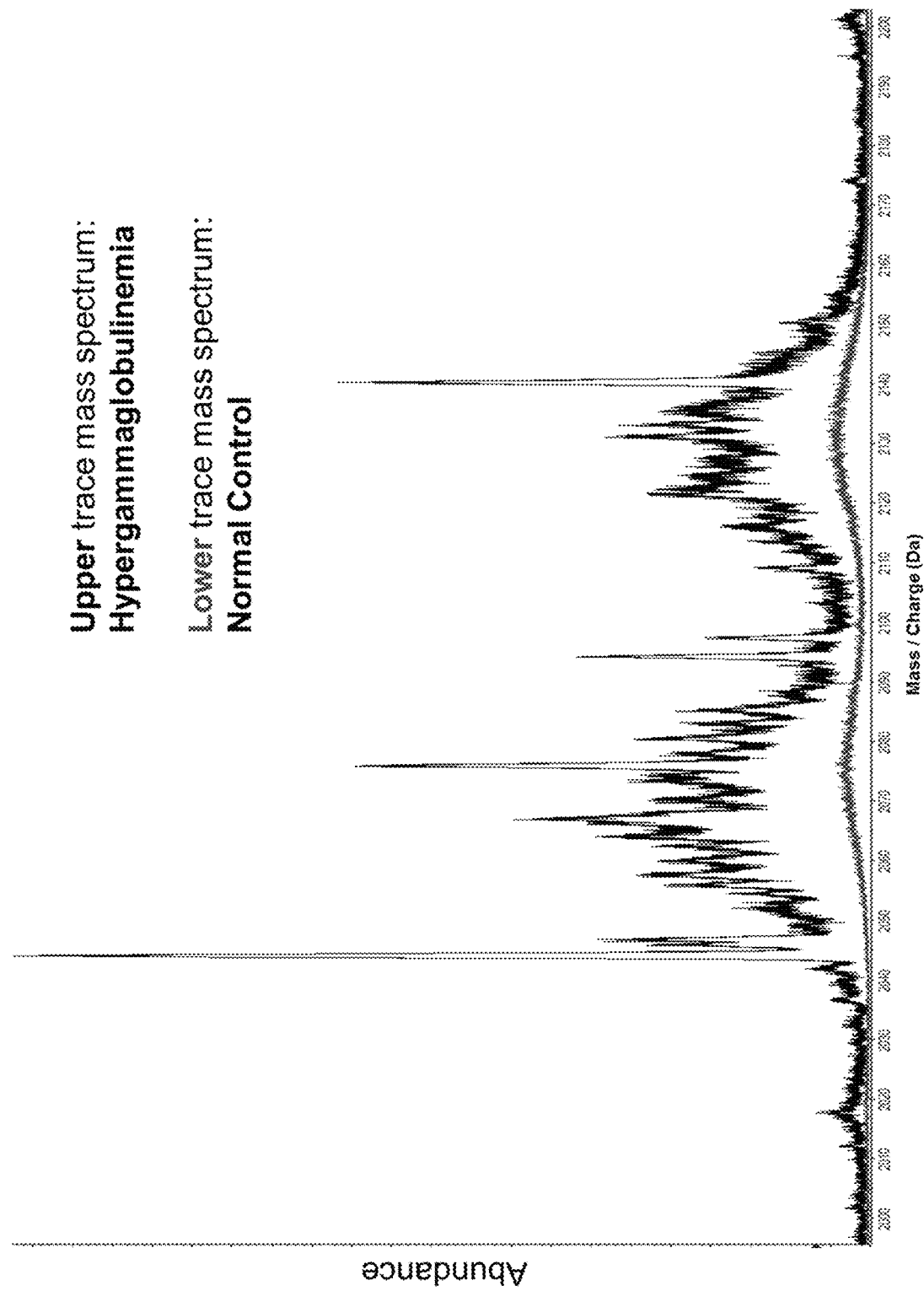
FIG. 9 shows the +11 charge state kappa and lambda light chain ions observed from serum taken from a patient with hypergammaglobulinemia (upper trace) compared to a normal control serum (lower trace).

Example 4—Ratios of Kappa and Lambda Light Chains in Patients with Various Disorders Serum samples from patients having various disorders were examined using the methods described above. Specifically, the light chain profiles of serum patients with high levels of total serum immunoglobulins often referred to as polyclonal gammopathy or hypergammaglobulinemia were tested. FIG. 9 shows the +11 charge state kappa and lambda light chain ions observed from serum taken from a patient with hypergammaglobulinemia (upper trace) compared to a normal control serum (lower trace). The mass spectra were acquired by summing all the spectra from the elution time of immunoglobulin light chains (data not shown). Upon comparison, it can be seen that the overall abundance of light chains is approximately 2-fold higher in the serum from the patient with hypergammaglobulinemia as compared to the serum from the normal control. In addition, the spectra from the hypergammaglobulinemia patient exhibits distinct monoclonal light chains present above the polyclonal background resulting in an oligoclonal appearance to the spectrum.

Figure 10:
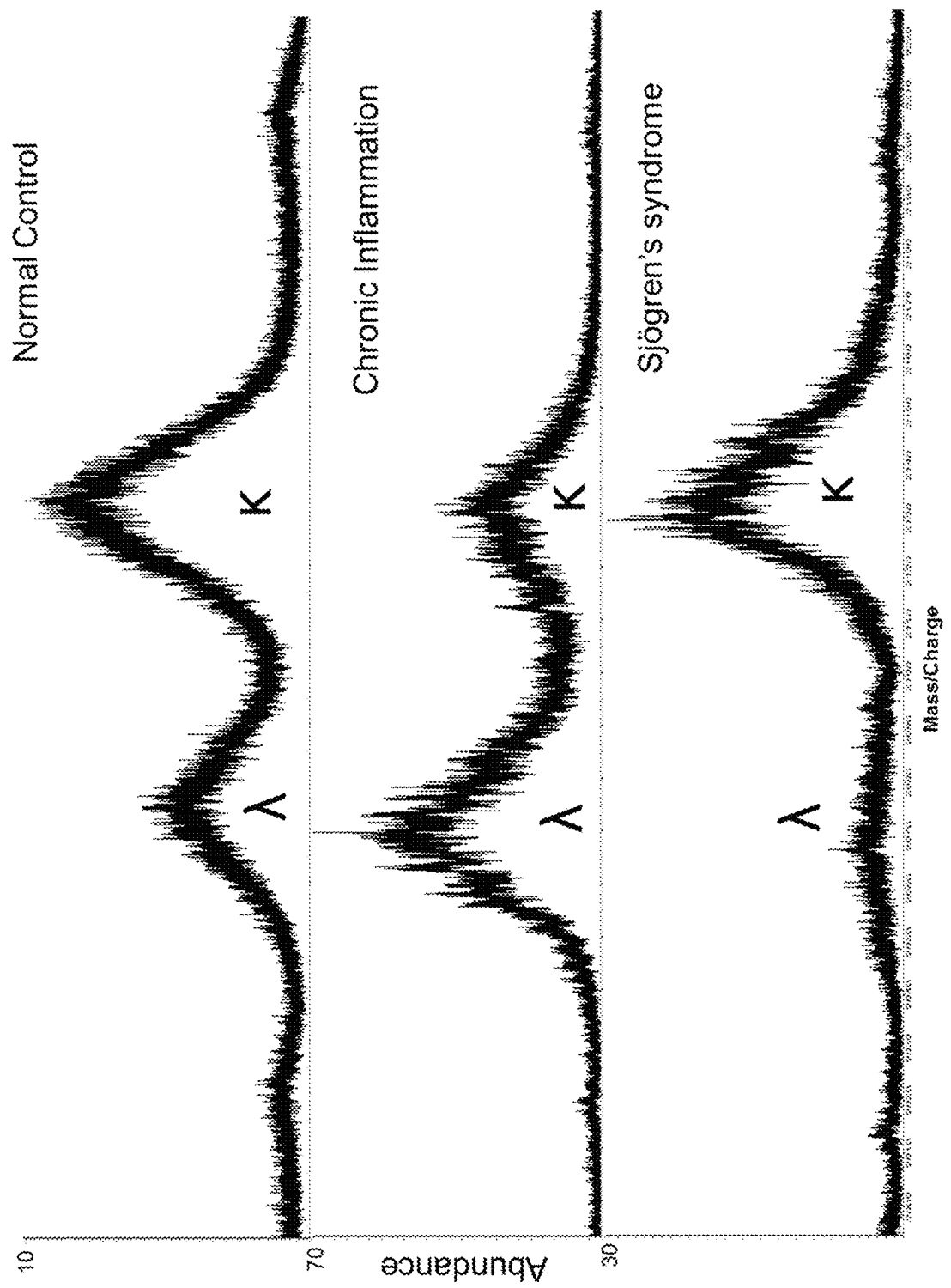
FIG. 10 shows the +11 charge state ions observed from normal control serum (top), a patient with a chronic inflammatory response of unknown origin (middle), and a patient with Sjögren's syndrome an autoimmune disorder involving the salivary and lacrimal glands (bottom).

Several other serum samples from patients with hypergammaglobulinemia were analyzed that showed a skewed kappa/lambda light chain molecular mass ratio. FIG. 10 shows the +11 charge state ions observed from normal control serum (top), a patient with a chronic inflammatory response of unknown origin (middle), and a patient with Sjögren's syndrome an autoimmune disorder involving the salivary and lacrimal glands (bottom). The profile in the middle from the patient with chronic inflammation shows that the overall abundance of lambda light chains is greater than the abundance of kappa light chains. The calculated peak area of the kappa light chains was found to be $4.05 \times 10^5$ while the lambda light chains was found to be $7.44 \times 10^5$ resulting in a kappa/lambda ratio of 0.54 or 35:65, nearly the opposite of the kappa/lambda ratio observed in the normal control serum. The profile from the patient with Sjögren's syndrome shows the predominance of kappa light chains. The calculated peak area of the kappa light chains was found to be $1.05 \times 10^5$ while the calculated peak area for the lambda light chains was found to be $2.10 \times 10^4$ resulting in a kappa/lambda ratio of 5 or 83:17.

Example 5—Identifying Light Chains in Samples with a Monoclonal Antibody

Experiments were also performed using normal serum spiked with the monoclonal recombinant therapeutic antibody HUMIRA® (adalimumab) which has a kappa light chain and an IgG heavy chain. FIG. 11 shows the response observed for the light chain from an LC-MS analysis performed as described above. The top of the figure shows the multiply charged light chain ions with the multiply charged HUMIRA kappa light chain ions with their different charge states highlighted. The bottom of FIG. 11 shows the molecular masses found when the multiply charged ions in the m/z spectrum are converted to their accurate molecular mass in Daltons (Da). The findings demonstrate that the kappa light chain from HUMIRA spiked into normal serum at 0.01 g/dL (100 mg/L) can be identified above the polyclonal background at a molecular mass of 23,407 Da. This molecular mass matches the mass of the HUMIRA kappa light chain.

Example 6—Sample from a Patient with a Monoclonal Gammopathy

Figure 12:
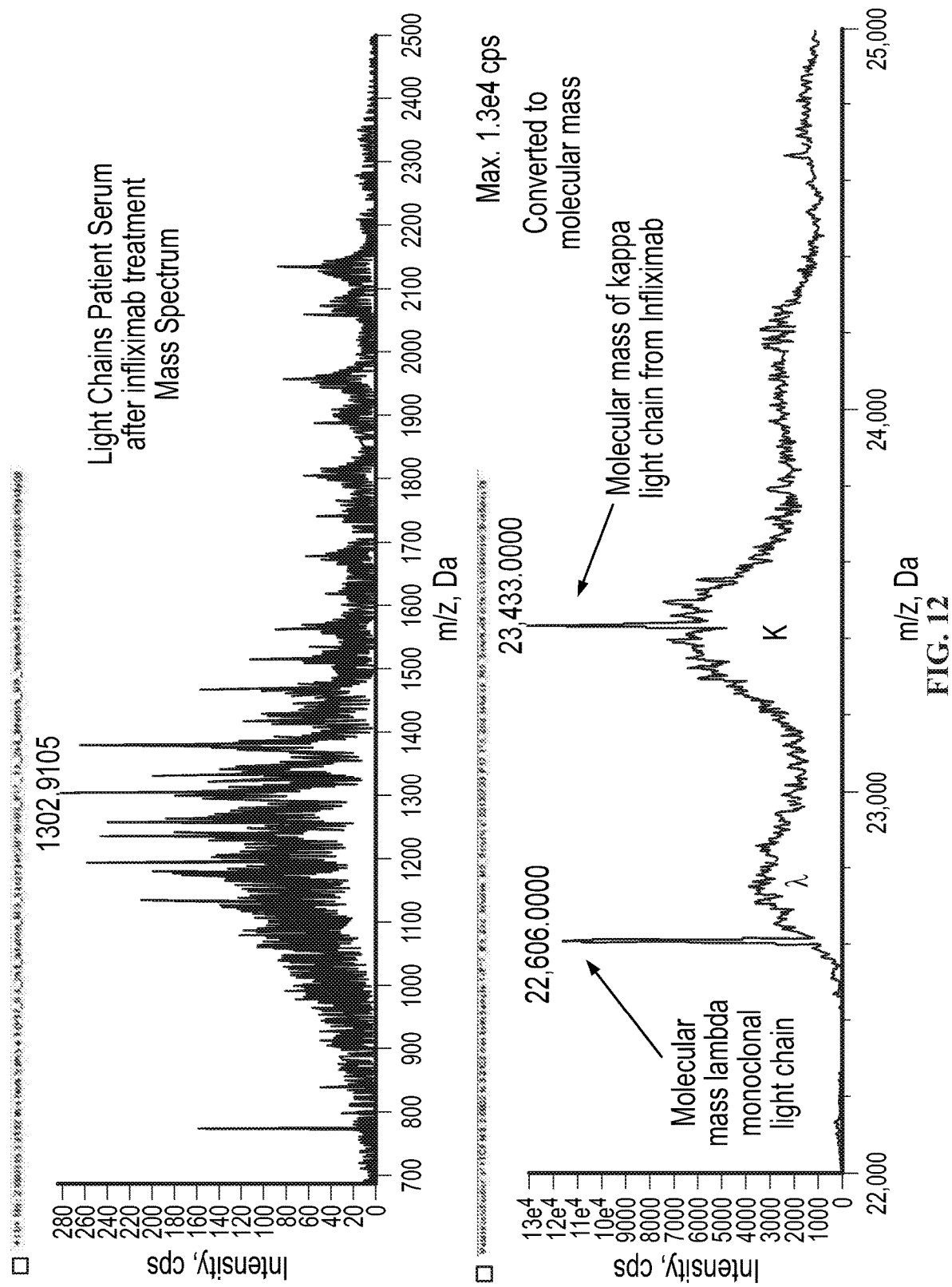
FIG. 12 shows the response observed in the light chain mass region for a serum sample from a patient with a known lambda monoclonal free light chain and who had also been treated with the monoclonal recombinant therapeutic antibody REMICADE® (infliximab) which has a kappa light chain and an IgG heavy chain.

Experiments were also performed using serum from a patient with a known lambda monoclonal free light chain and who had also been treated with the monoclonal recombinant therapeutic antibody REMICADE® (infliximab) which has a kappa light chain and an IgG heavy chain. FIG. 12 shows the response observed for the light chains from an LC-MS analysis performed as described above. The top of the figure shows the multiply charged light chain ions from the endogenous monoclonal lambda light chain and the kappa light chain from REMICADE. The bottom of FIG. 12 shows the molecular masses found when the multiply charged ions in the m/z spectrum are converted to their accurate molecular mass in Daltons (Da). The findings demonstrate that the endogenous monoclonal lambda light chain (22,606 Da) and the kappa light chain from the administered REMICADE (23,433 Da) are clearly visible above the polyclonal background. In addition, the endogenous lambda light chain is located within the lambda molecular mass distribution while the kappa light chain from Remicade is within the kappa molecular mass distribution with the correct molecular mass (24,433 Da).

Figure 13:
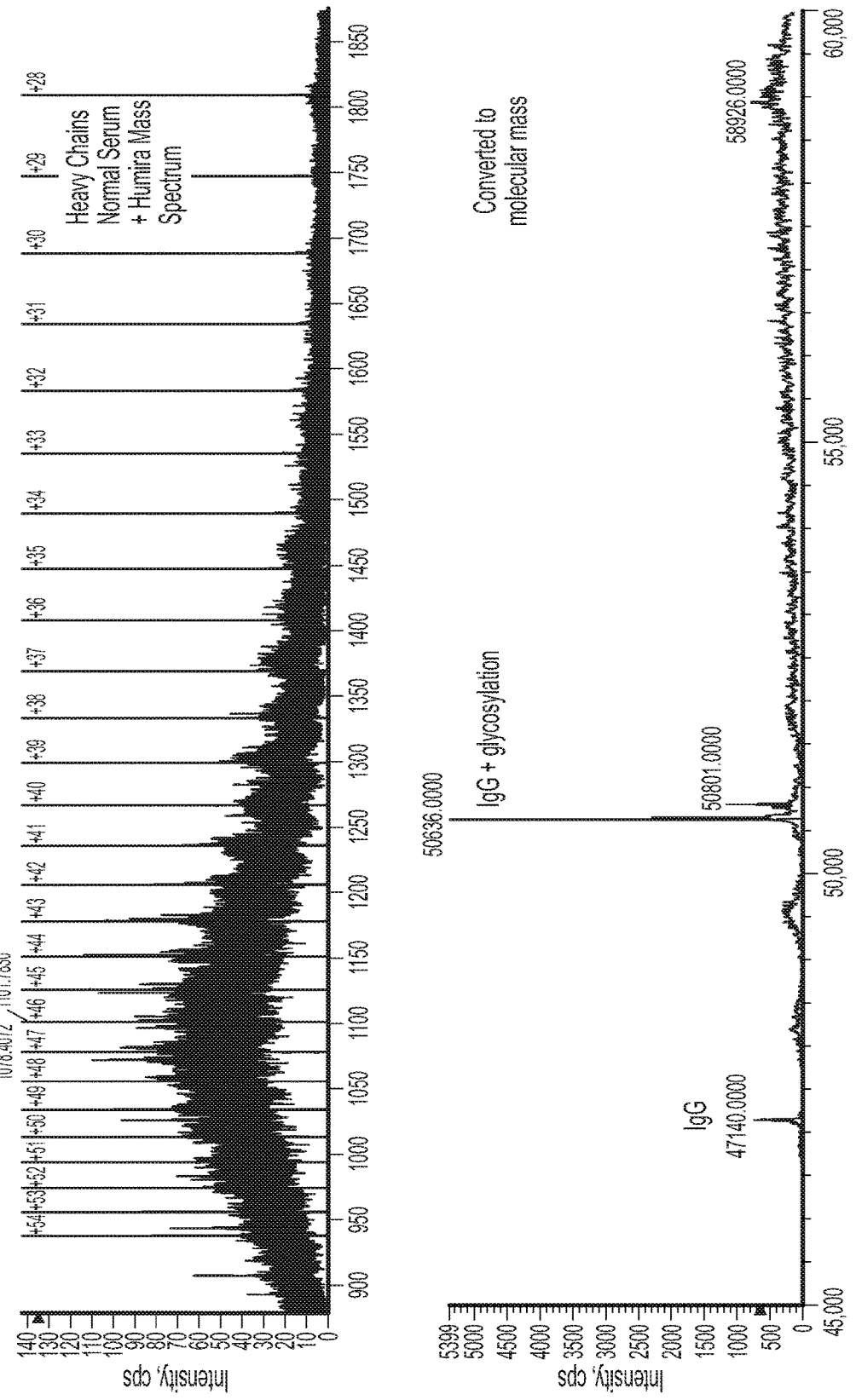
FIG. 13 shows the response observed in the heavy chain mass region for a serum sample spiked with the monoclonal recombinant therapeutic antibody HUMIRA® (adalimumab) which has a kappa light chain and an IgG heavy chain.

Example 7—Identifying Heavy Chains in Samples Spiked with a Monoclonal Antibody Experiments were performed using normal serum spiked with the monoclonal recombinant therapeutic antibody HUMIRA® (adalimumab) which has a kappa light chain and an IgG heavy chain. FIG. 13 shows the response observed for the heavy chain from an LC-MS analysis performed as described above. The top of the figure shows the multiply charged heavy chain ions with the multiply charged HUMIRA heavy chain ions with their different charge states highlighted. The bottom of FIG. 13 shows the molecular masses found when the multiply charged ions in the m/z spectrum are converted to their accurate molecular mass in Daltons (Da). The findings demonstrate that the IgG heavy chain from HUMIRA spiked into normal serum at 0.5 g/dL (5 g/L) can be identified above the polyclonal background at a molecular mass of 50,636 Da which correlates with the mass of the HUMIRA heavy chain with glycosylation. The non-glycosylated form is also observed at 47,140 Da. The method focuses on identifying a monoclonal immunoglobulin above the polyclonal background so as long as a glycoform associated with the monoclonal immunoglobulin is observed above the polyclonal background; the method is able to isotype the heavy chain by molecular mass.

Example 8

Figure 15:
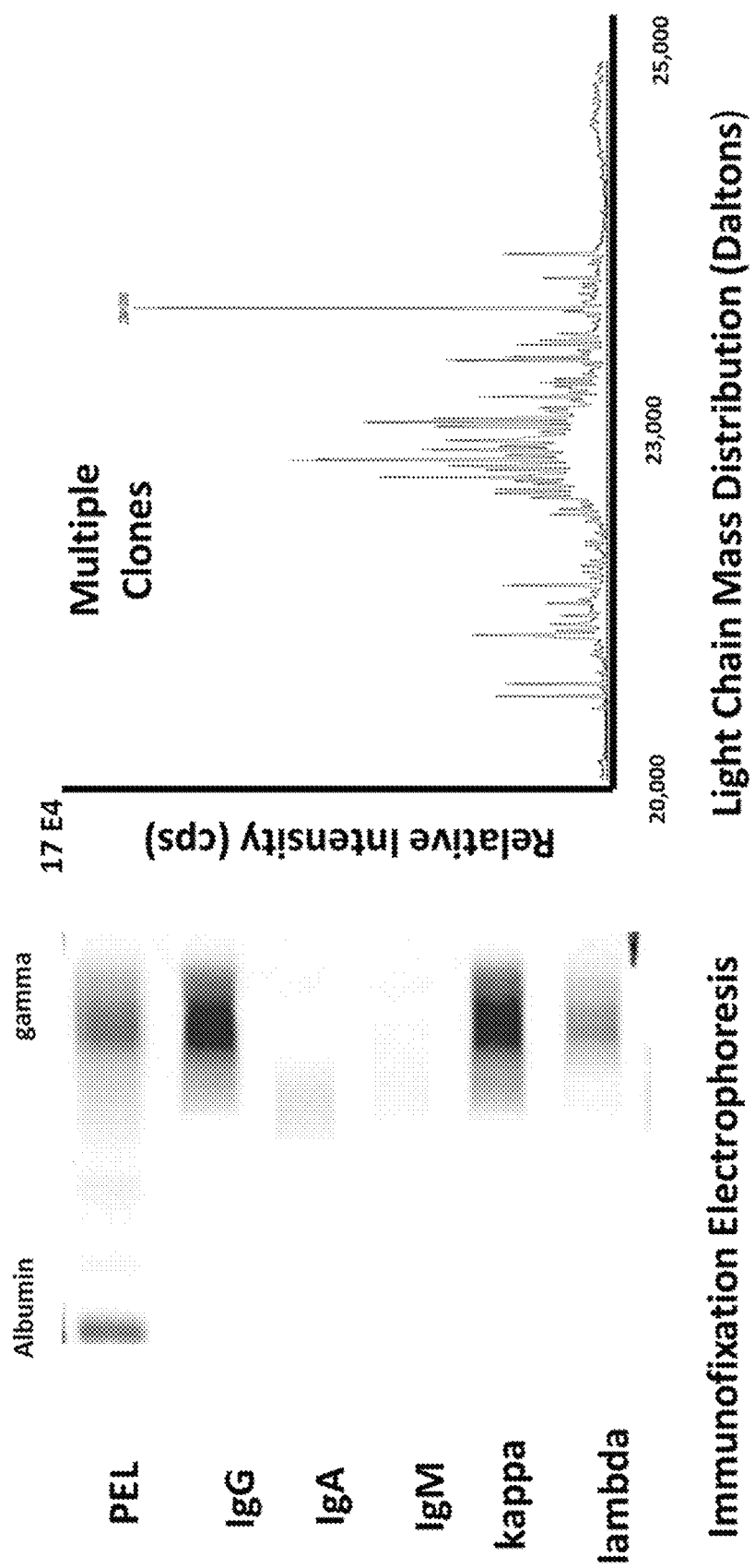
FIG. 15 shows the response observed in the light chain mass region for a serum sample from a patient with HIV infection.

A serum samples from an HIV infected patient was analyzed using a method as provided herein which demonstrated an oligoclonal immune response (FIG. 15). This type of distribution of clones is not possible by current gel based immunoglobulin characterization.

Example 9

CSF and Serum Samples.

Waste samples were collected from the Clinical Immunology Laboratory OCB assay.

Isoelectric Focusing Gel Electrophoresis Followed by IgG Immunoblotting (IgG IEF) OCB Assay.

Standard operating procedures for performing the IgG IEF OCB assay developed by the Clinical Immunology Laboratory were followed and reagent sets from Helena Laboratories (Beaumont, Tex.) were used.

Reagents.

Ammonium bicarbonate, dithiothreitol (DTT), and formic acid were purchased from Sigma-Aldrich (St. Louis, Mo.). Melon Gel was purchased from Thermo-Fisher Scientific (Waltham Mass.). Water, acetonitrile, and 2-propanol were purchased from Honeywell Burdick and Jackson (Muskegon, Mich.). Kappa and lambda monoclonal light chains purified from human urine were purchased from Bethyl Laboratories (Montgomery, Tex.).

CSF Preparation for Mass Spectrometry Assay.

A volume of 20 µL of CSF was reduced by adding 20 µL of 200 mM DTT solubilized in 50 mM ammonium bicarbonate buffer, pH 8.0, then incubated at 55° C. for 30 minutes. Samples were placed into 96 deep-well PCR plates (300 µL volume) at 9° C. while waiting for injection.

Serum Preparation for Mass Spectrometry Assay.

A volume of 20 µL of serum was enriched for immunoglobulins using 180 µL of Melon Gel and then 20 µL of sample was reduced by adding DTT as previously described. See Barnidge D R, Dasari S, Botz C M, et al. Using Mass Spectrometry to Monitor Monoclonal Immunoglobulins in Patients with a Monoclonal Gammopathy. J Proteome Res. 2014 Feb. 11.

Liquid Chromatography.

An Eksigent MicroLC 200 Plus System (Foster City, Calif.) was used to separate immunoglobulins prior to ionization and detection on an ABSciex TripleTOF 5600 quadrupole time-of-flight mass spectrometer (ABSciex, Vaughan ON, Canada) as previously described. See Barnidge D R, Dasari S, Botz C M, et al. Using Mass Spectrometry to Monitor Monoclonal Immunoglobulins in Patients with a Monoclonal Gammopathy. J Proteome Res. 2014 Feb. 11.

MS Data Analysis.

Analyst TF v1.6 was used for instrument control. Data were viewed using Analyst TF v1.6 and PeakView v1.2. The mass spectra used for analysis were obtained by summing all mass spectra over the known LC retention times for light chains. The peak centroid of specific charge states m/z value was used to assess the abundance of a specific monoclonal immunoglobulin in CSF and serum as previously described. See, Barnidge D R, Dasari S, Ramirez-Alvarado M, et al. Phenotyping polyclonal kappa and lambda light chain molecular mass distributions in patient serum using mass spectrometry. J Proteome Res. 2014 Nov. 7; 13(11):5198-205 Accurate molecular calculations were performed by deconvoluting all multiple charged ions from the protein using BioAnalyst™.

Results.

Figure 16:
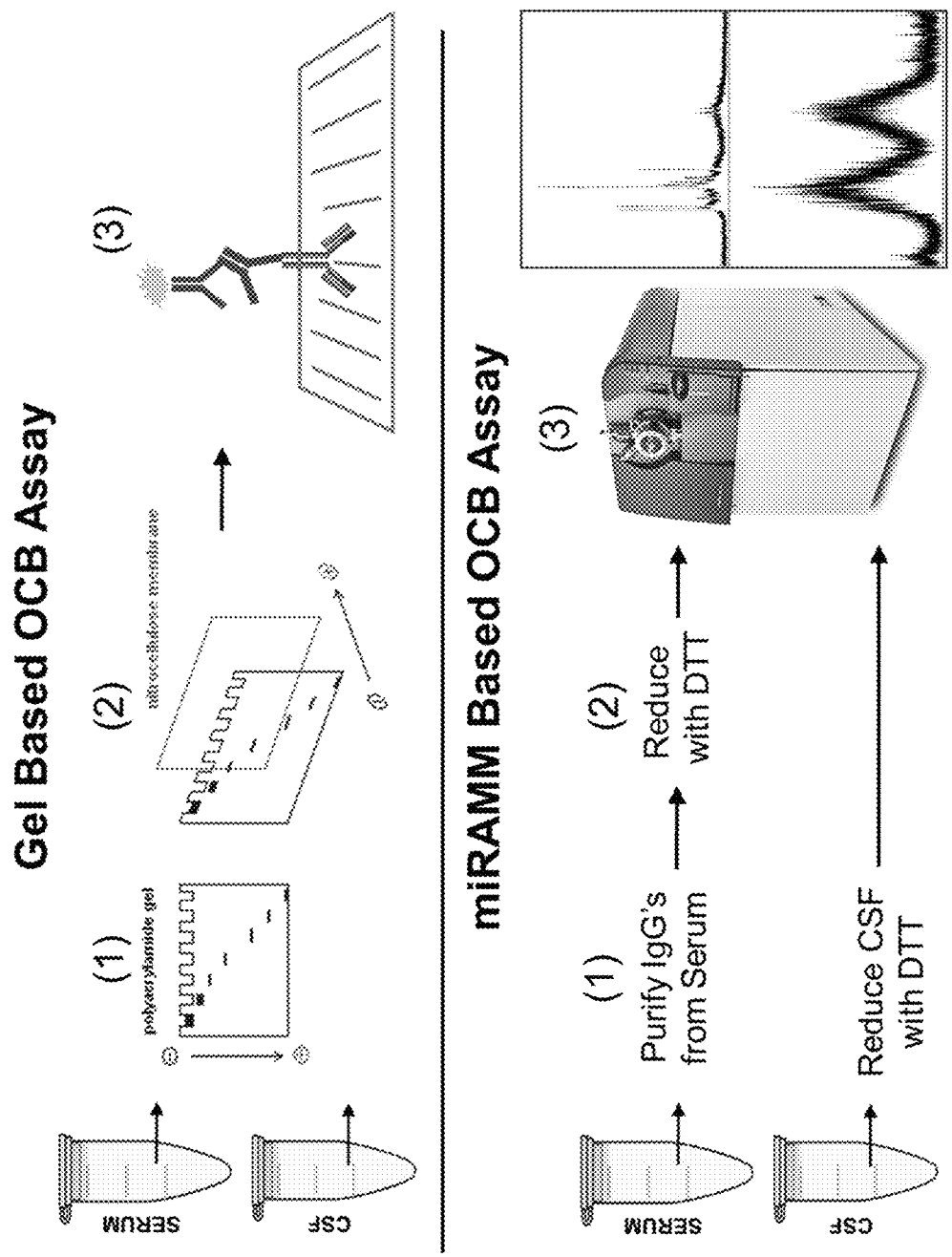
FIG. 16 illustrates the steps in the sample preparation for a gel based method (top) and a mass spectrometry based method (bottom) as provided herein.
Figure 17:
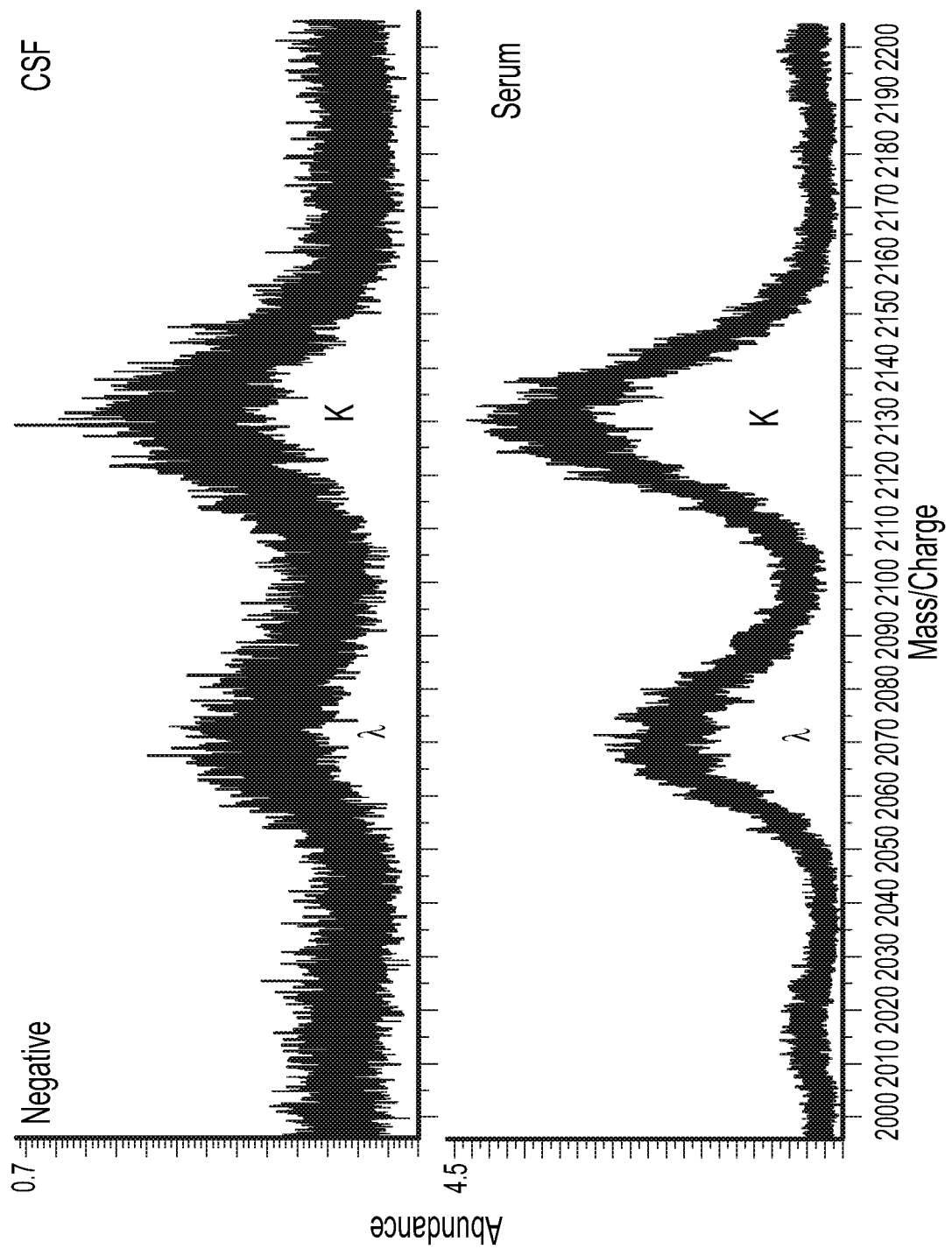
FIG. 17 illustrates mass spectra from a patient negative for CSF specific monoclonal immunoglobulins by IgG IEF analyzed by a mass spectrometry based method (bottom), as provided herein.
Figure 18:
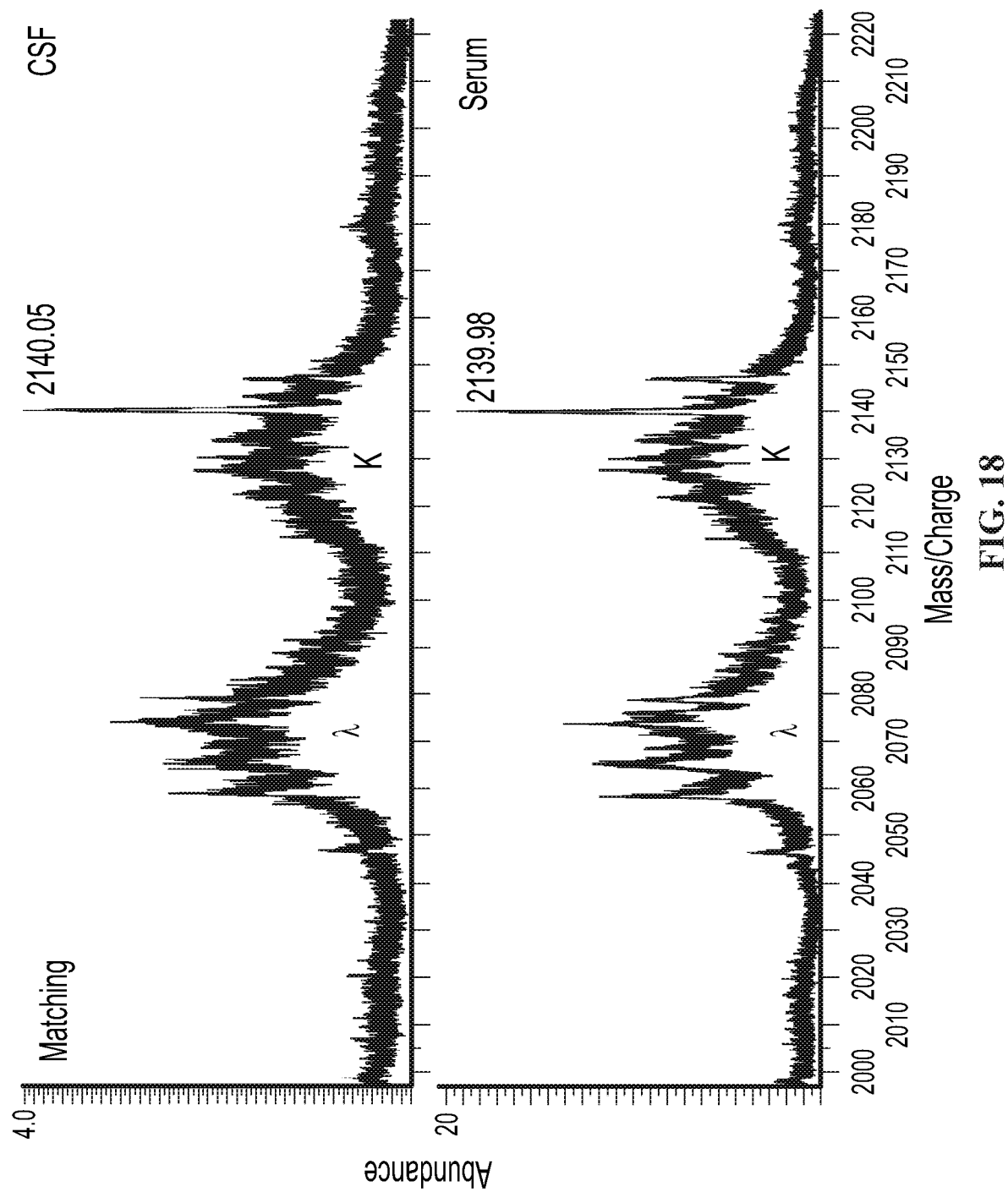
FIG. 18 illustrates mass spectra from a patient with matching CSF and serum monoclonal immunoglobulins (i.e. a negative patient) by IgG IEF analyzed by a mass spectrometry based method, as provided herein.
Figure 19:
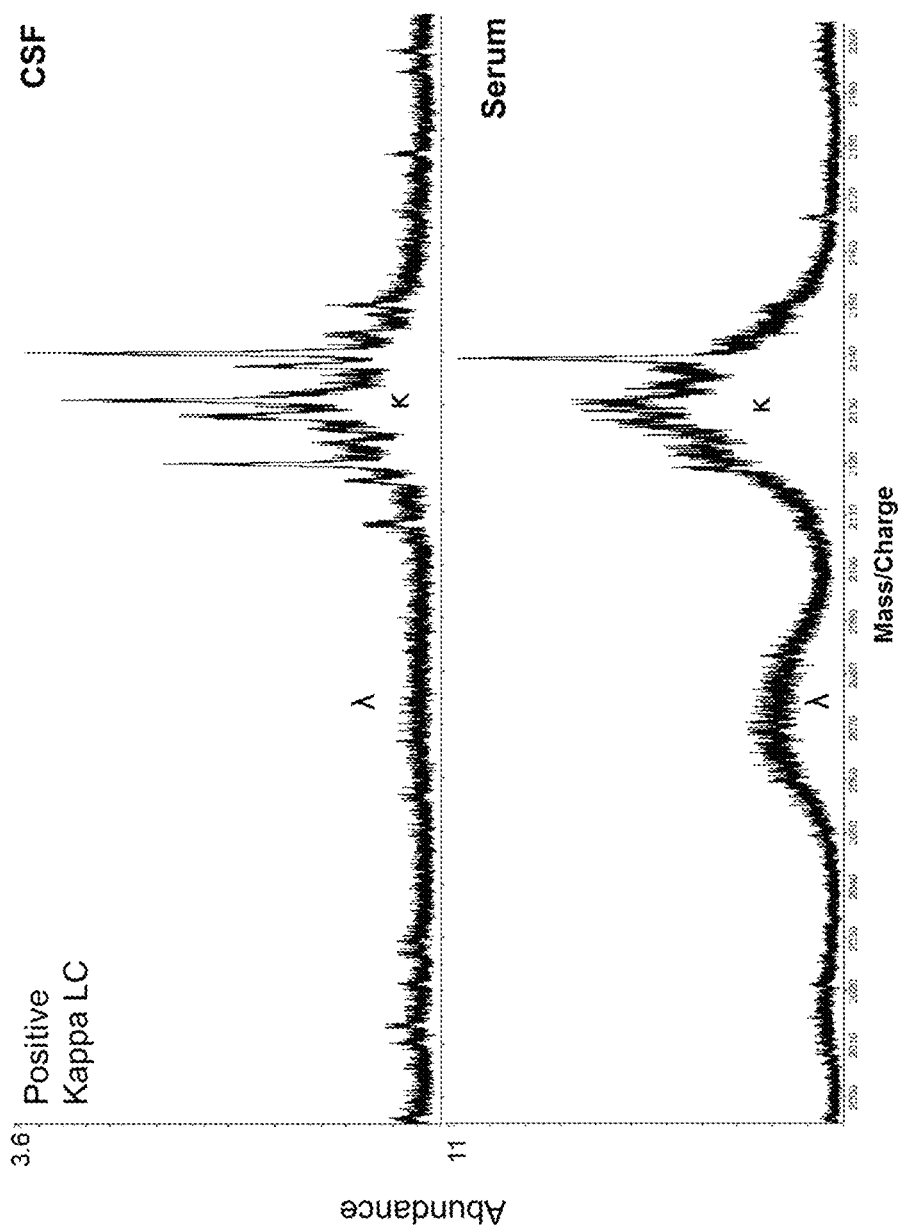
FIG. 19 illustrates mass spectra from a patient positive for CSF specific monoclonal immunoglobulins by IgG IEF analyzed by a mass spectrometry based method, as provided herein.
Figure 20:
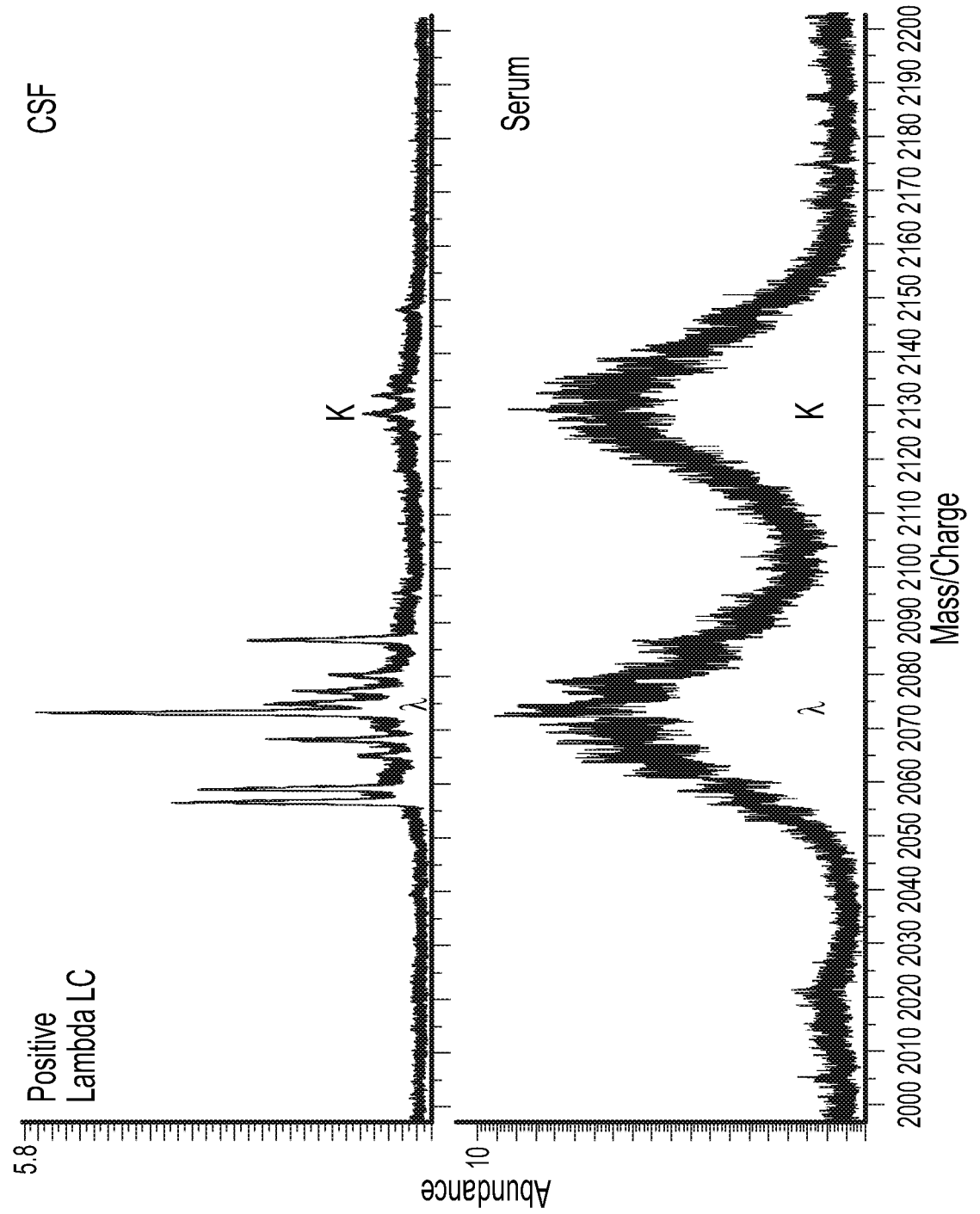
FIG. 20 illustrates mass spectra from a patient positive for CSF specific monoclonal immunoglobulins by IgG IEF analyzed by a mass spectrometry based method, as provided herein.

FIG. 16 illustrates the steps in the gel based and mass spectrometry based OCB assays. The gel assay (top of FIG. 16) used IEF gel electrophoresis (1), followed by passive nitrocellulose blotting (2) anti-IgG antibodies, and secondary antibodies to visualize IgGs (3). The process is manual and takes several hours to complete. The mass spectrometry assay uses Melon Gel to enrich serum samples for IgG while CSF samples are diluted 1:1 (1). Both samples are reduced with DTT prior to analysis by microLC-ESI-Q-TOF MS (3). The entire process is automatable and takes 1 hour. FIG. 17 shows the miRAMM results for matched CSF and serum acquired from a patient that was negative for OCB by IgG IEF. The figure shows the normally distributed polyclonal kappa and lambda molecular mass distributions for the +11 charge state from reduced light chains. FIG. 18 shows the miRAMM results for matched CSF and serum from a patient with matching CSF and serum OCB by IgG IEF. Multiple kappa and lambda light chains are observed above the polyclonal background in both samples. The large band detected in the kappa light chain region of the CSF had a calculated molecular mass of 23,529.37 Da while the light chain found in the serum had a calculated molecular mass of 23,528.75 Da, a difference of 0.62 Da. These findings demonstrate the exceptional specificity of miRAMM for matching "bands" in CSF and serum. The ability of miRAMM for identifying CSF specific clones is shown FIG. 19 and FIG. 20. FIG. 19 shows the miRAMM results for matched serum and CSF from a patient with kappa OCB bands unique to CSF by IgG IEF while FIG. 20 shows the miRAMM results for matched serum and CSF from a patient with lambda OCB bands unique to CSF by IgG IEF. The two figures clearly demonstrate the presence of multiple clonal light chain peaks in the CSF sample that are not present in the serum sample.

Figure 21:
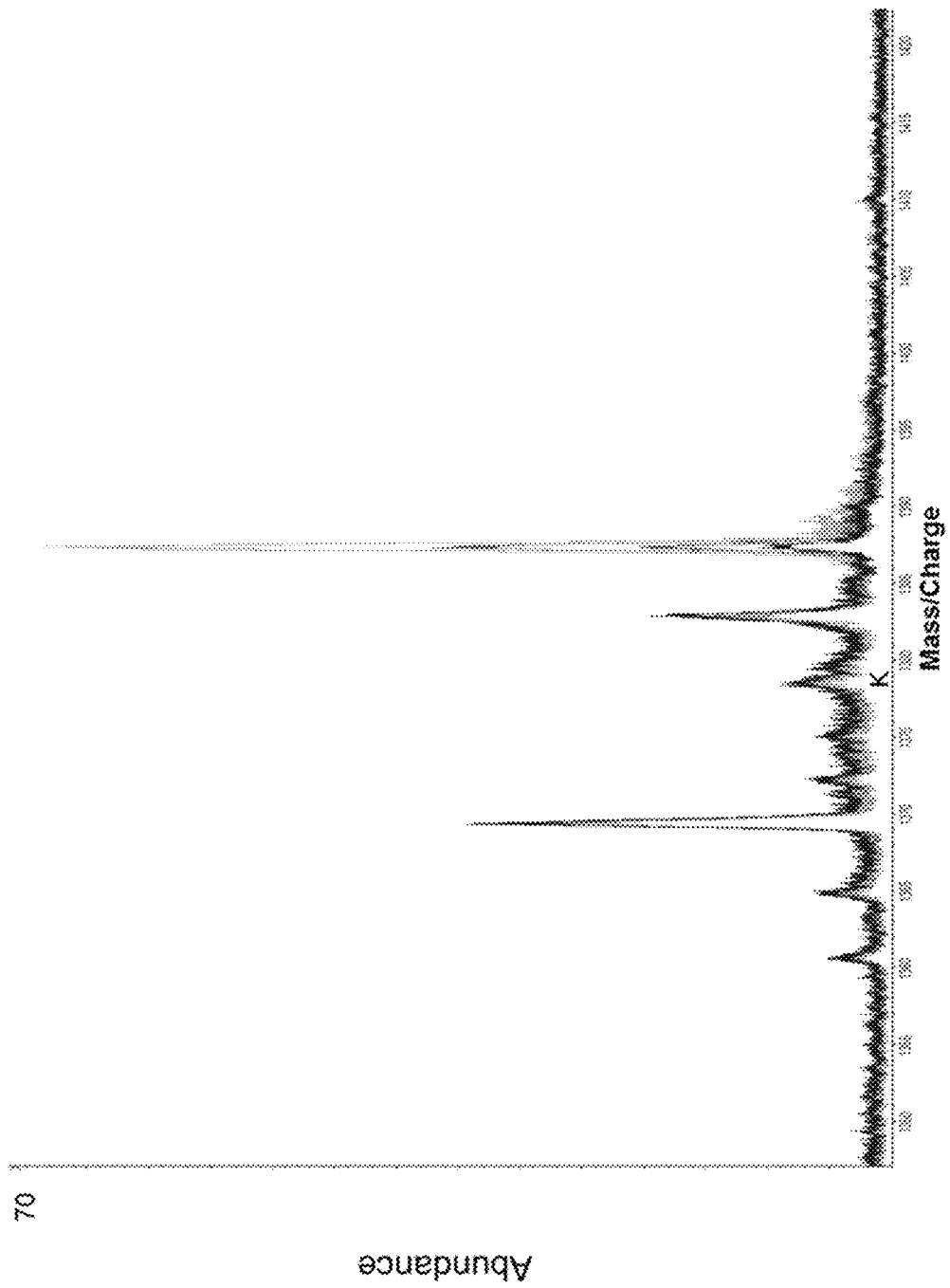
FIG. 21 illustrates the +17 charge state kappa light chains from a patient CSF sample positive for OCB that was spiked with a kappa light chain standard then analyzed by a mass spectrometry based method, as provided herein. The blue trace is the 1.5 µg/mL spike, the pink trace is the 3 µg/mL spike, the orange trace is the 6 µg/mL spike, and the green trace is the 12 µg/mL spike.

A cohort of 56 patients was analyzed by miRAMM to compare its performance to OCB by IgG IEF. If multiple clonal light chains were uniquely identified in the CSF with a signal to noise ratio greater than 3, the sample was called positive. The cohort contained 24 positive and 32 negative IgG IEF OCB results. When the patients were blindly analyzed by miRAMM the same patients were recorded as; 22 positive, 34 negative. The 2 discordant did have apparent clonal light chains in the CSF by miRAMM but the abundance of these light chains was slightly below the S/N cut-off of 3.

miRAMM can also be used to quantitate immunoglobulins. Purified monoclonal kappa and lambda light chain standards were diluted into an OCB-positive CSF. Dilution series were made using the kappa or lambda light chain ranging from 1 to 50 µg/mL. The peak areas for the kappa and lambda standards diluted linearly with R2 values of 0.999 and 0.992. Inter- and intra-day precision was calculated using an OCB-positive CSF, and the intra-day precision from 20 replicates was 8.1% while the inter-day precision calculated over 10 days was 12.8%. The mass spectrum in FIG. 21 shows overlaid mass spectra from four different concentrations of kappa light chain standard spiked into a CSF sample. The kappa light chain standard peak shown in the green trace is the 12.5 µg/mL standard while the blue trace represents the 1.5 µg/mL standard. The change in the abundance of each kappa light chain standard is seen next to the fixed abundance of the patient's own kappa light chains.

Example 10

Methods.

Five hundred fifty six (556) serum samples that had been previously analyzed by routine clinical PEL/IFE testing were evaluated by MADLI-TOF MS (Microflex LT, Bruker Daltonics). Prior to analysis, intact immunoglobulins were isolated from serum with Capture Select™ (Hu)LC-kappa and LC-lambda affinity resin (Life Technologies) and reduced with tris(2-carboxyethyl)phosphine hydrochloride (TCEP-HCl, Thermo Scientific). Purified samples were prepared for MALDI-TOF analysis using dried droplet method and α-cyano-4-hydroxycinnamic acid as matrix. Mass analysis was performed in positive ion mode with summation of 500 laser shots.

Results.

For spectral analysis, the ion distribution of the MH+1 and MH+2 charge states of the light chain were compared to the spectrum of normal serum. Any monoclonal abnormalities were distinguished from the normal pattern. Of the 556 samples assayed, abnormal patterns were identified in 406 of 421 samples (96%) that were positive by IFE. Abnormalities were also noted in 23 of 126 samples (18%) that were negative by IFE. Of the 9 samples that were indeterminate by IFE, abnormalities were noted in 2.

Example 11

Mass spectra were generated by analyzing proteins eluted from single domain antibody fragments with affinity for different immunoglobulin isotypes. Briefly, the mass spectra used to derive the isotype specific m/z distributions for each isotype were generated from 43 healthy adult serum samples. Samples were diluted 10-fold with 1×PBS (100 µL patient sample+900 µL of 1×PBS). 10 µL of each single-domain antibody fragment (targeting the IgG, IgA, IgM, kappa and lambda constant region) coupled to agarose beads (50% beads+50% 1×PBS) were added to 200 µL of the dilute sample and incubated for 30 minutes at RT. The supernatant was removed from the beads. The beads were then washed two times in 200 µL of 1×PBS and then two times in 200 µL of water. Then 80 µL of 5% Acetic Acid with 50 mMTCEP was added to the beads and incubated for 5 minutes at RT. Then 0.6 µL of supernatant was spotted on each well on a 96-well MALDI plate which was spotted with 0.6 µL of matrix (α-cyano-4-hydroxycinnamic acid). Subsequently, another 0.6 µL of matrix is spotted on top of the sample. Mass analysis is performed in positive ion mode with summation of 500 laser shots using a MALDI-TOF mass spectrometer. A mass/charge (m/z) range of 9,000 to 32,000 m/z is acquired. Next, the mass spectrum generated for each SDAF was overlaid and M-proteins were detected and isotyped by the presence of distinct peaks with specific m/z regions occupied by the light chain and heavy chain repertoire.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for detecting immunoglobulin heavy chains in a sample, the method comprising:
   a) providing a biological sample comprising immunoglobulins, paired immunoglobulin heavy and light chains, or mixtures thereof;
   b) immunopurifying the sample, wherein the immunopurifying comprises using an antibody selected from the group consisting of an anti-human IgG antibody, an anti-human IgA antibody, an anti-human IgM antibody, an anti-human IgD antibody, an anti-human IgE antibody, and combinations thereof;
   c) subjecting the immunopurified sample to a decoupling step wherein immunoglobulin light chains are decoupled from immunoglobulin heavy chains; and
   d) subjecting the decoupled sample to a mass spectrometry technique to obtain a mass spectrum of the sample, said mass spectrum comprising one or more peaks corresponding to one or more intact immunoglobulin heavy chains in the sample; wherein said one or more peaks quantify the amount of the one or more intact immunoglobulin heavy chains in the sample.

2. The method of claim 1, wherein the antibody is a non-human antibody.

3. The method of claim 2, wherein the non-human antibody is at least one of a camelid antibody, a cartilaginous fish antibody, llama, sheep, goat, or a mouse antibody.

4. The method of claim 3, wherein the antibody is a single domain antibody fragment (SDAF).

5. The method of claim 4, wherein the SDAF is derived from a camelid antibody, a cartilaginous fish antibody, llama, a mouse antibody, sheep, goat, or a human antibody.

6. The method of claim 5, wherein the SDAF is selected such that the mass spectrum generated in step c) for the single domain antibody fragment does not overlap with the mass spectrum generated in step c) for the immunoglobulin light chain or immunoglobulin heavy chain.

7. The method of claim 6, wherein the SDAF is selected such that the SDAF generates a signal of about 12,500 to about 15,000 m/z in step c) with a single charge.

8. The method of claim 1, wherein the sample comprising immunoglobulin light chains, immunoglobulin heavy chains, or mixtures thereof is analyzed as a single fraction in a single analysis.

9. The method claim 1, further comprising determining the pairing of immunoglobulin heavy chains and immunoglobulin light chains in the sample.

10. The method of claim 1, further comprising determining the quantitative amount of one or more of the immunoglobulin heavy chains in the sample.

11. The method claim 1, further comprising identifying a M-protein in the sample.

12. The method of claim 11, further comprising quantifying the M-protein in the sample.

13. The method of claim 12, further comprising determining the pairing of immunoglobulin heavy chains and immunoglobulin light chains in the M-protein in the sample.

14. A method for detecting immunoglobulin heavy chains in a sample, the method comprising:
a) providing a biological sample comprising immunoglobulins, paired immunoglobulin heavy and light chains, or mixtures thereof,
b) immunopurifying the sample utilizing a single domain antibody fragment (SDAF) having affinity for an immunoglobulin, wherein said SDAF is selected from the group consisting of an anti-human IgG SDAF, an anti-human IgA SDAF, an anti-human IgM SDAF, an anti-human IgD SDAF, an anti-human IgE SDAF, an anti-human kappa SDAF, an anti-human lambda SDAF, and combinations thereof;
c) subjecting the immunopurified sample to a decoupling step where light chain immunoglobulins are decoupled from the heavy chain immunoglobulins;
wherein one or more of the immunoglobulin light chains or immunoglobulin heavy chains is derived from an M-protein;
d) subjecting the immunopurified sample to a mass spectrometry technique to obtain a mass spectrum of the sample, said mass spectrum comprising one or more peaks corresponding to one or more intact immunoglobulin light chains in the sample; wherein said one or more peaks quantify the amount of the one or more intact immunoglobulin heavy chains in the sample,
wherein the mass spectrometry technique is chosen from the group consisting of (i) liquid chromatography electrospray ionization coupled to mass analyzer (ii) a microflow liquid chromatography electrospray ionization coupled to a quadrupole time-of-flight mass spectrometry technique and (iii) a matrix assisted laser adsorption ionization-time of flight mass spectrometry technique; and
e) determining one or more of (i) the identity of the M-protein, (ii) the quantity of the M-protein, (iii) the pairing of immunoglobulin heavy chains and immunoglobulin light chains of the M-protein, and (iv) the quantitative amount of one or more of the immunoglobulin heavy chains and M-protein in the sample.

15. The method of claim 14, wherein the SDAF is derived from a camelid antibody, a cartilaginous fish antibody, llama, a mouse antibody, sheep, goat, or a human antibody.

16. The method of claim 15, wherein the SDAF is selected such that the mass spectrum generated in step d) for the SDAF does not overlap with the mass spectrum generated in step d) for the immunoglobulin light chain or immunoglobulin heavy chain.

17. The method of claim 16, wherein the SDAF is selected such that the SDAF generates a signal of about 12,500 to about 15,000 m/z in step d) with a single charge.

18. A method for monitoring treatment of a disorder in a subject, said method comprising:
a) providing a biological sample obtained from the subject, wherein the biological sample comprises immunoglobulins, paired immunoglobulin heavy and light chains, or mixtures thereof;
b) immunopurifying the sample, wherein the immunopurifying comprises using an antibody selected from the group consisting of an anti-human IgG antibody, an anti-human IgA antibody, an anti-human IgM antibody, an anti-human IgD antibody, an anti-human IgE antibody, and combinations thereof;
c) subjecting the immunopurified sample to a decoupling step wherein immunoglobulin light chains are decoupled from immunoglobulin heavy chains; and
d) subjecting the decoupled sample to a mass spectrometry technique to obtain a mass spectrum of the sample, said mass spectrum comprising one or more peaks corresponding to one or more intact immunoglobulin heavy chains or one or more intact immunoglobulin light chains in the sample; wherein said one or more peaks quantify the amount of the one or more intact immunoglobulin heavy chains or one or more intact immunoglobulin light chains in the sample.

19. The method of claim 18, wherein the treatment comprises administering a therapeutic monoclonal antibody to the subject, and wherein said one or more peaks that quantify the amount of the one or more intact immunoglobulin heavy chains or one or more intact immunoglobulin light chains are from said therapeutic monoclonal antibody.

20. The method of claim 18, wherein said biological sample is selected from the group consisting of a whole blood sample, a serum sample, a plasma sample, a urine sample, and a cerebrospinal fluid sample.

* * * * *

SEQUENCE LISTING

<160> NUMBER OF SEQ ID NOS: 5

<210> SEQ ID NO 1
<211> LENGTH: 107
<212> TYPE: PRT
<213> ORGANISM: Homo sapiens

<400> SEQUENCE: 1

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Val Val Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 2
<211> LENGTH: 105
<212> TYPE: PRT
<213> ORGANISM: Homo sapiens

<400> SEQUENCE: 2

Gln Pro Lys Ala Asn Pro Thr Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Gly Ser Pro Val
        35                  40                  45

Lys Ala Gly Val Glu Thr Ile Lys Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 3
<211> LENGTH: 105
<212> TYPE: PRT
<213> ORGANISM: Homo sapiens

<400> SEQUENCE: 3

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Ile Thr Pro Ser Lys Gln Ser Asn Asn Lys
    50                  55                  60

```
Tyr Ala Ala Ser Ser Tyr Leu Ser Leu Thr Pro Glu Gln Trp Lys Ser
 65                  70                  75                  80

His Arg Ser Tyr Ser Cys Gln Val Thr His Glu Gly Ser Thr Val Glu
                 85                  90                  95

Lys Thr Val Ala Pro Thr Glu Cys Ser
            100                 105

<210> SEQ ID NO 4
<211> LENGTH: 105
<212> TYPE: PRT
<213> ORGANISM: Homo sapiens

<400> SEQUENCE: 4

Gln Pro Lys Ala Ala Pro Ser Val Thr Leu Phe Pro Pro Ser Ser Glu
 1               5                  10                  15

Glu Leu Gln Ala Asn Lys Ala Thr Leu Val Cys Leu Ile Ser Asp Phe
                20                  25                  30

Tyr Pro Gly Ala Val Thr Val Ala Trp Lys Ala Asp Ser Ser Pro Val
            35                  40                  45

Lys Ala Gly Val Glu Thr Ile Thr Pro Ser Lys Gln Ser Asn Asn Lys
 50                  55                  60

Tyr Ala Ala Ser Ser Tyr Leu Ser Leu Thr Pro Glu Gln Trp Lys Ser
 65                  70                  75                  80

His Lys Ser Tyr Ser Cys Gln Val Thr His Glu Gly Ser Thr Val Glu
                 85                  90                  95

Lys Thr Val Ala Pro Thr Glu Cys Ser
            100                 105

<210> SEQ ID NO 5
<211> LENGTH: 106
<212> TYPE: PRT
<213> ORGANISM: Homo sapiens

<400> SEQUENCE: 5

Gln Pro Lys Ala Ala Pro Ser Val Thr Leu Phe Pro Pro Ser Ser Glu
 1               5                  10                  15

Glu Leu Gln Ala Asn Lys Ala Thr Leu Val Cys Leu Val Met Ser Asp
                20                  25                  30

Phe Tyr Pro Gly Ala Val Thr Val Ala Trp Lys Ala Asp Gly Ser Pro
            35                  40                  45

Val Lys Val Gly Val Glu Thr Thr Lys Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Arg Val Thr His Glu Gly Ser Thr Val
                 85                  90                  95

Glu Lys Thr Val Ala Pro Ala Glu Cys Ser
            100                 105
```